(12) United States Patent
Deng et al.

(10) Patent No.: US 10,236,920 B2
(45) Date of Patent: Mar. 19, 2019

(54) SIGNAL TRANSMITTER AND METHODS FOR TRANSMITTING SIGNALS FROM ANIMALS

(71) Applicant: Battelle Memorial Institute, Richland, WA (US)

(72) Inventors: Z. Daniel Deng, Richland, WA (US); Jun Lu, Richland, WA (US); Huidong Li, Richland, WA (US); Chuan Tian, Richland, WA (US); Mitchell J. Myjak, Richland, WA (US); Brian J. Bellgraph, Richland, WA (US); Sam Cartmell, Richland, WA (US); Jie Xiao, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/087,936

(22) Filed: Mar. 31, 2016

(65) Prior Publication Data

US 2017/0170850 A1 Jun. 15, 2017

Related U.S. Application Data

(60) Provisional application No. 62/267,797, filed on Dec. 15, 2015.

(51) Int. Cl.
*H04M 1/00* (2006.01)
*H04B 1/034* (2006.01)
(Continued)

(52) U.S. Cl.
CPC ............ *H04B 1/034* (2013.01); *A01K 11/006* (2013.01); *A01K 11/008* (2013.01); *A01K 61/90* (2017.01);
(Continued)

(58) Field of Classification Search
CPC .... H04B 1/034; H04M 4/382; H04M 4/5835; A01K 11/008; A01K 99/00
(Continued)

(56) References Cited

U.S. PATENT DOCUMENTS

| 3,100,866 A | 8/1963 | Marks |
| 3,262,093 A | 7/1966 | Junger et al. |

(Continued)

FOREIGN PATENT DOCUMENTS

| CA | 2091043 | 9/1994 |
| CN | 1424592 | 8/2003 |

(Continued)

OTHER PUBLICATIONS

WO PCT/US2014/053578 Inv-Pay Fees, dated Dec. 5, 2014, Battelle Memorial Institute.
(Continued)

*Primary Examiner* — Sanh D Phu
(74) *Attorney, Agent, or Firm* — Wells St. John P.S.

(57) ABSTRACT

Injectable transmitters are provided that can include a body with the body housing a power source and an oscillator, the injectable transmitter also including an antenna extending from the body, the body and antenna being of sufficient size to be injected through a 9 gauge needle. Radio frequency transmitters are provided that can include a body extending from a nose to a tail with the body housing a power source and RF signal generator components. The power source of the transmitter can define at least a portion of the nose of the body. The transmitters can have an antenna extending from the tail. Methods for attaching a radio frequency (RF) transmitter to an animal are provided. The methods can include providing an RF transmitter and providing an injection device having a needle of gauge of 9 or smaller; providing the RF transmitter into the injection device; and
(Continued)

providing the RF transmitter through the 9 gauge or smaller needle and into the animal.

6 Claims, 20 Drawing Sheets

(51) Int. Cl.
| | |
|---|---|
| A01K 11/00 | (2006.01) |
| A01K 99/00 | (2006.01) |
| H01M 4/38 | (2006.01) |
| H01M 4/583 | (2010.01) |
| G01S 1/02 | (2010.01) |
| A01K 61/90 | (2017.01) |
| G06K 19/07 | (2006.01) |
| G06K 19/077 | (2006.01) |
| H04B 1/38 | (2015.01) |
| A61B 5/00 | (2006.01) |
| A61B 5/11 | (2006.01) |

(52) U.S. Cl.
CPC .............. *A01K 99/00* (2013.01); *G01S 1/02* (2013.01); *G06K 19/0723* (2013.01); *G06K 19/07762* (2013.01); *H01M 4/382* (2013.01); *H01M 4/5835* (2013.01); *A61B 5/1112* (2013.01); *A61B 5/6861* (2013.01); *A61B 2503/40* (2013.01); *H01M 2220/30* (2013.01); *H04B 2001/3894* (2013.01)

(58) Field of Classification Search
USPC ...................................................... 455/575.1
See application file for complete search history.

(56) References Cited

U.S. PATENT DOCUMENTS

| | | | |
|---|---|---|---|
| 3,311,830 A | 3/1967 | Skirvin | |
| 3,576,732 A | 4/1971 | Weidinger et al. | |
| 3,713,086 A | 1/1973 | Trott | |
| 4,042,845 A | 8/1977 | Hackett | |
| 4,241,535 A | 12/1980 | Tsukuda | |
| 4,259,415 A * | 3/1981 | Tamura | H01M 4/36 |
| | | | 429/231.5 |
| 4,353,004 A | 10/1982 | Kleinschmidt | |
| 4,392,236 A | 7/1983 | Sandstrom et al. | |
| 4,679,559 A | 7/1987 | Jefferts | |
| 4,762,427 A * | 8/1988 | Hori | G01N 27/18 |
| | | | 374/141 |
| 4,790,090 A | 12/1988 | Sharber | |
| 4,970,988 A | 11/1990 | Heisey | |
| 4,986,276 A | 1/1991 | Wright | |
| 5,177,891 A | 1/1993 | Holt | |
| 5,211,129 A * | 5/1993 | Taylor | A01K 11/006 |
| | | | 119/200 |
| 5,324,940 A | 6/1994 | Ekstrom | |
| 5,344,357 A | 9/1994 | Lyczek | |
| 5,517,465 A | 5/1996 | Nestler et al. | |
| 5,675,555 A | 10/1997 | Evans et al. | |
| 5,697,384 A * | 12/1997 | Miyawaki | A01K 11/007 |
| | | | 128/899 |
| 5,974,304 A | 10/1999 | Chen | |
| 5,995,451 A | 11/1999 | Evans et al. | |
| 6,201,766 B1 | 3/2001 | Carlson et al. | |
| 6,662,742 B2 | 12/2003 | Shelton et al. | |
| 6,712,772 B2 | 3/2004 | Cohen et al. | |
| 7,016,260 B2 | 3/2006 | Baray | |
| 7,289,931 B2 | 10/2007 | Ebert | |
| 7,457,720 B2 | 11/2008 | Ebert | |
| 8,032,429 B2 | 10/2011 | Shafer | |
| 8,033,890 B2 | 10/2011 | Warner et al. | |
| 8,360,327 B2 | 1/2013 | Clarke | |
| 8,564,985 B2 | 10/2013 | van Straaten | |
| 9,266,591 B2 | 2/2016 | Lu | |
| 2003/0117893 A1 | 6/2003 | Baray | |
| 2003/0128847 A1 | 7/2003 | Smith | |
| 2006/0218374 A1 | 9/2006 | Ebert | |
| 2007/0088194 A1 | 4/2007 | Tahar et al. | |
| 2007/0103314 A1 | 5/2007 | Giessler | |
| 2007/0288160 A1 | 12/2007 | Ebert | |
| 2009/0073802 A1 | 3/2009 | Nizzola et al. | |
| 2009/0079368 A1 | 3/2009 | Poppen et al. | |
| 2009/0188320 A1 | 7/2009 | Greenough et al. | |
| 2011/0105829 A1 | 5/2011 | Ball | |
| 2011/0163857 A1 | 7/2011 | August et al. | |
| 2011/0181399 A1 | 7/2011 | Pollack et al. | |
| 2011/0254529 A1 | 10/2011 | van Straaten | |
| 2012/0134239 A1 | 5/2012 | Struthers | |
| 2012/0277550 A1 | 11/2012 | Rosenkranz et al. | |
| 2013/0012865 A1* | 1/2013 | Sallberg | A61M 5/32 |
| | | | 604/21 |
| 2013/0181839 A1 | 7/2013 | Cao | |
| 2013/0324059 A1 | 12/2013 | Lee et al. | |
| 2014/0211594 A1 | 7/2014 | Allen et al. | |
| 2015/0063072 A1 | 3/2015 | Deng et al. | |
| 2015/0241566 A1 | 8/2015 | Chakraborty et al. | |
| 2015/0289479 A1 | 10/2015 | Allen et al. | |
| 2016/0211924 A1 | 7/2016 | Deng et al. | |
| 2016/0245894 A1 | 8/2016 | Deng et al. | |
| 2017/0089878 A1 | 3/2017 | Deng et al. | |
| 2017/0164581 A1 | 6/2017 | Deng et al. | |
| 2018/0055007 A1 | 3/2018 | Deng et al. | |

FOREIGN PATENT DOCUMENTS

| | | |
|---|---|---|
| CN | 102568463 | 7/2012 |
| CN | 102598716 | 7/2012 |
| CN | 202414143 | 9/2012 |
| CN | 102754249 | 10/2012 |
| CN | 2014800479315 | 7/2017 |
| EP | 2037396 A1 | 3/2009 |
| EP | 1705500 B1 | 6/2010 |
| GB | 2188028 A | 9/1987 |
| WO | WO 95/03691 | 2/1995 |
| WO | WO 2011/068825 | 6/2011 |
| WO | WO 2011/079338 | 7/2011 |
| WO | WO 2015/031853 | 3/2015 |
| WO | WO PCT/US2015/062200 | 2/2016 |
| WO | WO PCT/US2015/062200 | 8/2017 |
| WO | WO PCT/US2017/038082 | 9/2017 |
| WO | WO PCT/US2017/038082 | 11/2017 |
| WO | WO PCT/US2016/054981 | 6/2018 |
| WO | WO PCT/US2016/055045 | 8/2018 |

OTHER PUBLICATIONS

WO PCT/US2014/053578 IPRP, dated Mar. 1, 2016, Battelle Memorial Institute.

WO PCT/US2014/053578 Search Rept., dated Mar. 5, 2015, Battelle Memorial Institute.

WO PCT/US2014/053578 Writ. Opin., dated Mar. 5, 2015, Battelle Memorial Institute.

Aktakka et al., "Energy Scavenging from Insect Flight", Journal of Micromechanics and Microengineering vol. 21, 095016, 2011, United Kingdom, 10 pages.

Brown et al., "An Evaluation of the Maximum Tag Burden for Implantation of Acoustic Transmitters in Juvenile Chinook Salmon", North American Journal of Fisheries Management vol. 30, 2010, United States, pp. 499-505.

Cha et al., "Energy Harvesting from a Piezoelectric Biomemetic Fish Tail", Renewable Energy vol. 86, 2016, Netherlands, pp. 449-458.

Cha et al., "Energy Harvesting from the Tail Beating of a Carangiform Swimmer using Ionic Polymer-Metal Composites", Bioinspiration and Biomimetics vol. 8, 2013, United Kingdom. 15 pages.

(56) References Cited

OTHER PUBLICATIONS

Cook et al., "A Comparison of Implantation Methods for Large PIT Tags or Injectable Acoustic Transmitters in Juvenile Chinook Salmon", Fisheries Research vol. 154, 2014, Netherlands, pp. 213-223.
Dagdeviren et al., "Conformal Piezoelectric Energy Harvesting and Storage from Motions of the Heart, Lung, and Diaphragm", Proceedings of the National Academy of Sciences of the United States of America vol. 111, 2014, United States, pp. 1927-1932.
Deng et al., "A Cabled Acoustic Telemetry System for Detecting and Tracking Juvenile Salmon: Part 2. Three-Dimensional Tracking and Passage Outcomes", Sensors vol. 11, 2011, Switzerland, pp. 5661-5676.
Deng et al., "An Injectable Acoustic Transmitter for Juvenile Salmon", Scientific Reports, Jan. 29, 2015, United Kingdom, 6 pages.
Deng et al., "Design and Instrumentation of a Measurement and Calibration System for an Acoustic Telemetry System", Sensors vol. 10, 2010, Switzerland, pp. 3090-3099.
Deng et al., U.S. Appl. No. 14/914,974, filed Feb. 26, 2016, titled "Acoustic Transmission Devices and Process for Making and Using Same", 82 pages.
Deng et al., U.S. Appl. No. 15/088,032, filed Mar. 31, 2016, titled "Transmitters for Animals and Methods for Transmitting from Animals", 57 pages.
Deng et al., U.S. Appl. No. 62/267,738, filed Dec. 15, 2015, titled "Transmitters for Animals and Methods for Transmitting from Animals", 42 pages.
Eppard, "Juvenile Salmon Acoustic Telemetry System JSATS", Dec. 14. 2011, URL: http://www.nwcouncil.org/media/23478/jsats.pdf, pp. 1-13.
Erturk et al., "Underwater Thrust and Power Generation Using Flexible Piezoelectric Composites: An Experimental Investigation Toward Self-Powered Swimmer-Sensor Platforms", Smart Materials and Structures vol. 20, 125013, 2011, United Kingdom, 11 pages.
Hwang et al., "Self-PoweredCardiac Pacemaker Enabled by Flexible Single Crystalline PMN-PT Piezoelectric Energy Harvester", Advanced Materials vol. 26, 2014, Germany, pp. 4880-4887.
Hwang et al., "Self-Powered Deep Brain Stimulation via a Flexible PIMNT Energy Harvester", Energy and Environmental Science vol. 8, 2015, United Kingdom, pp. 2677-2684.
Lam et al., "Physical Characteristics and Rate Performance of (CFx)n (0.33<x<9,66) in Lithium Batteries", Journal of Power Sources vol. 153, 2006, Netherlands, pp. 354-359.
Li et al., "Design Parameters of a Miniaturized Piezoelectric Underwater Acoustic Transmitter", Sensors vol. 12, 2012, Switzerland, pp. 9098-9109.
Li et al., "Energy Harvesting from Low Frequency Applications using Piezoelectric Materials", Applied Physics Reviews 1, 041301, 2014, United States, 20 pages.
Li et al., "Piezoelectric Materials Used in Underwater Acoustic Transducers" Sensor Letters vol. 10 (3/4), 2012, United States, pp. 679-697.
Li et al., "Piezoelectric Transducer Design for a Miniaturized Injectable Acoustic Transmitter", Smart Materials and Structures vol. 24, 115010, 2015, United Kingdom, 9 pages.
McMichael et al., "The Juvenile Salmon Acoustic Telemetry System: A New Tool", Fisheries vol. 35, No. 1, Jan. 1, 2010, United States, pp. 9-22.
Meduri et al., "Hybrid CVx-Ag2V4O11 as a High-Energy, Power Density Cathode for Application in an Underwater Acoustic Microtransmitter", Electrochemistry Communications vol. 13, 2011, United States, pp. 1344-1348.
Ritchie et al., "Further Developments of Lithium/Polycarbon Monofluoride Envelope Cells", Journal of Power Sources vol. 96, 2001, Netherlands, pp. 180-183.
Rub et al., "Comparative Performance of Acoustic-Tagged and Passive Integrated Transponder-Tagged Juvenile Salmonids in the Columbia and Snake Rivers", U.S. Army Corps of Engineers, Portland District, Portland Oregon, 2007, United States, 163 pages.

S.M. Corporation, "Macro Fiber Composite—MFC" Smart Material Brochure, United States, 8 pages.
Shafer, "Energy Harvesting and Wildlife Monitoring", available online at http://www.ofwim.org/wp-content/uploads/2014/11/ Shafer_keynote.pdf, 2014, 36 pages.
Weiland et al., "A Cabled Acoustic Telemetry System for Detecting and Tracking Juvenile Salmon: Part 1. Engineering Design and Instrumentation", Sensors vol. 11, No. 12, Dec. 26, 2011, Switzerland, pp. 5645-5660.
Yazami et al., "Fluorinated Carbon Nanofibres for High Energy and High Power Densities Primary Lithium Batteries", Electrochemistry Communications vol. 9, 2007, United States, pp. 1850-1855.
Zhang et al., "Enhancement of Discharge Performance of Li/CFx Cell by Thermal Treatment of CFx Cathode Material", Journal of Power Sources vol. 188, 2009, Netherlands, pp. 601-605.
GB1195633 A, Derwent Summary, dated Jun. 17, 1970, VartaAG.
Brown, "Design Considerations for Piezoelectric Polymer Ultrasound Transducers", IEEE Transactions on Ultrasonics, Ferroelectrics, and Frequency Control vol. 47, No. 6, Nov. 2000, United States, pp. 1377-1396.
Brown, "The Effects of Material Selection for Backing and Wear Protection/Quarter-Wave Matching of Piezoelectric Polymer Ultrasound Transducers", IEEE Ultrasonics Symposium, 2000, United States, pp. 1029-1032.
Cada, "The Development of Advanced Hydroelectric Turbines to Improve Fish Passage Survival", Fisheries vol. 26, No. 9, Sep. 2001, United States, pp. 14-23.
Carlson et al., "Sensor Fish Characterization of Spillway Conditions at Ice Harbor Dam in 2004, 2005 and 2006", PNWD-3839 Final Report, Mar. 2008, United States, 95 pages.
Carlson et al., "The Sensor Fish—Making Dams More Salmon-Friendly", Sensors Online, Jul. 2004, United States, 7 pages.
Coutant, "Fish Behavior in Relation to Passage Through Hydropower Turbines: A Review", Transactions of the American Fisheries Society vol. 129, 2000, United States, pp. 351-380.
Deng et al., "Design and Implementation of a New Autonomous Sensor Fish to Support Advanced Hydropower Development", Review of Scientific Instruments vol. 85, 2014, United States, 6 pages.
Deng et al., "Evaluation of Fish-Injury Mechanisms During Exposure to Turbulent Shear Flow", Canadian Journal of Fisheries and Aquatic Sciences vol. 62, 2005, Canada, pp. 1513-1522.
Deng et al., "Six-Degree-of-Freedom Sensor Fish Design and Instrumentation", Sensors vol. 7, 2007, United States, pp. 3399-3415.
Deng et al., "Use of an Autonomous Sensor to Evaluate the Biological Performance of the Advanced Turbine at Wanapum Dam", Journal of Renewable and Sustainable Energy vol. 2, 2010, United States, 11 pages.
Johnson et al., "A Digital Acoustic Recording Tag for Measuring the Response of Wild Marine Mammals to Sound", IEEE Journal of Oceanic Engineering vol. 28, No. 1, Jan. 2003, United States, pp. 3-12.
Kogan et al., "Acoustic Concentration of Particles in Piezoelectric Tubes: Theoretical Modeling of the Effect of Cavity Shape and Symmetry Breaking", The Journal of the Acoustical Society of America vol. 116, No. 4, 2004, United States, pp. 1967-1974.
Odeh, "A Summary of Environmentally Friendly Turbine Design Concepts", DOE/ID/13741 Paper, Jul. 1999, United States, 47 pages.
Richmond et al., "Response Relationships Between Juvenile Salmon and an Autonomous Sensor in Turbulent Flow", Fisheries Research vol. 97, 2009, Netherlands, pp. 134-139.
Deng et al., U.S. Appl. No. 14/871,761, filed Sep. 30, 2015, titled "Autonomous Sensor Fish to Support Advanced Hydropower Development", 41 pages.
WO PCT/US2016/054981 Search Rept., dated Nov. 18, 2016, Battelle Memorial Institute.
WO PCT/US2016/054981 Writ. Opin., dated Nov. 18, 2016, Battelle Memorial Institute.
WO PCT/US2016/055045 Search Rept., dated Feb. 7, 2017, Battelle Memorial Institute.

(56) References Cited

OTHER PUBLICATIONS

WO PCT/US2016/055045 Writ. Opin., dated Feb. 7, 2017, Battelle Memorial Institute.

Butler et al., "A Tri-Modal Directional Modern Transducer", Oceans 2003 MTS/IEEE Conference, Sep. 22-26, 2003, United States, pp. 1554-1560.

Carlson et al., "Juvenile Salmon Acoustic Telemetry System Transmitter Downsize Assessment", Pacific Northwest National Laboratory, Richland, WA, 2010, United States, 30 pages.

Dillon, "Use and Calibration of the Internal Temperature Indicator", Microchip Technology Inc. AN1333, 2010, United States, 12 pages.

El Rifai et al., "Modeling of Piezoelectric Tube Actuators", DspaceEMIT: Innovation in Manufacturing Systems and Technology (IMST), 2004, Singapore, 9 pages.

Lewandowski et al., "In Vivo Demonstration of a Self-Sustaining, Implantable, Stimulated-Muscle-Powered Piezoelectric Generator Prototype", Annals of Biomedical Engineering vol. 37, No. 11, Nov. 2009, Netherlands, pp. 2390-2401.

Pacific Northwest National Laboratory, "JSATS Tag Downsize Project Progess Report", PNNL, Apr. 26, 2010, United States, 16 pages.

Pacific Northwest National Laboratory, "Juvenile Salmon Acoustic Telemetry System (JSATS) Acoustic Transmitters", PNNL, Mar. 2010, United States, 1 page.

Platt et al., "The Use of Piezoelectric Ceramics for Electric Power Generation Within Orthopedic Implants", IEEE/ASME Transactions on Mechatronics vol. 10, No. 4, Aug. 2005, United States, pp. 455-561.

Rifai et al., "Modeling of Piezoelectric Tube Actuators", Dspace@MIT, available online at https://dspace.mit.edu/bitstream/handle/1721.1/3911/IMST014.pdf, 2004, 8 pages.

Adams et al., "Effects of Surgically and Gastrically Implanted Radio Transmitters on Swimming Performance and Predator Avoidance of Juvenile Chinook Salmon (Oncorhynchus tshawytscha)", Canadian Journal of Fisheries and Aquatic Sciences 55, 1998, Canada, pp. 781-787.

Anglea et al., "Effects of Acoustic Transmitters on Swimming Performance and Predator Avoidance of Juvenile Chinook Salmon", North American Journal of Fisheries Management 24, 2004, United States, pp. 162-170.

Atlantic States Marine Fisheries Commission, "American Eel Benchmark Stock Assessment Report No. 12-01", May 2012, United States, 340 pages.

Barns, "Behaviour and Swimming Performance of Elvers of the American Eel, Anguilla Rostrata, in an Experimental Flume", Journal of Fish Biology 45, 1994, United Kingdom, pp. 111-121.

Barbin et al., "Behaviour and Swimming Performance of Elvers of the American Eel, Anguilla Rostrata, in an Experimental Flume", Journal of Fish Biology 45, 1994, United Kingdom, pp. 111-121.

Biopack Systems, Inc. Hardware Guide, 2013, 152 pages.

Boubee et al., "Downstream Passage of Silver Eels at a Small Hydroelectric Facility", Fisheries Management and Ecology vol. 13, 2006, United Kingdom, pages 165-176.

Brett, "The Respiratory Metabolism and Swimming Performance of Young Sockeye Salmon", Journal of the Fisheries Board of Canada 21(5), 1964, Canada, pp. 1183-1226.

Brown et al., "Evidence to Challenge the "2% Rule" for Biotelemetry", North American Journal of Fisheries Management 19, 1999, United States, pp. 867-871.

Brown et al., "Survival of Seaward-Migrating PIT and Acoustics-Tagges Juvenile Chinook Salmon in the Snake and Columbia Rivers: An Evaluation of Length-Specific Tagging Effects", Animal Biotelemetry 1:8, 2013, United States, 13 pages.

Collins et al., "Intracoelomic Acoustic Tagging of Juvenile Sockeye Salmon: Swimming Performance, Survival, and Postsurgical Wound Healing in Freshwater and during a Transition in Seawater", Transactions of the American Fisheries Society 142, 2013, United States pp. 515-523.

Cote et al., "Swimming Performance and Growth Rates of Juvenile Atlantic Cod Inrapertoneatly Implanted with Dummy Acoustic Transitters", North American Journal of Fisheries Management vol. 19, 1999, United States, pp. 1137-1141.

Counihan et al., "Influence of Externally Attached Transmitters on the Swimming Performance of Juvenile White Sturgeon", Transations of the American Fisheries Society 128, 1999, United States, pp. 965-970.

Deng et al., U.S. Appl. No. 15/393,617, filed Dec. 29, 2016, titles "Systems and Methods for Monitoring Organisma Within an Aquatic Environment", 49 pages.

Dinwoodie, "Dual Output Boost Converter", Texas Instruments Application Report SLUA288, available online at http://www.ti.com.lit/an/slua288.pdf, Apr. 2003, 9 pages.

Fisheries and Oceans Canada (DFO), "Recovery Potential Assessment of American Eel (Anguilla rostrata) in Eastern Canada", Canadian Science Advisory Secrerariat Science Advisory Report 2013/078, 2013, Canada, 65 pages.

Gallego-Juarez et al., "Experimental Study of Nonlinearity in Free Progressive Acoustic Waves in Air at 20 kHz", Journal de Physique, Colloques, 40 (C8), 1979, France, pp. 336-340.

Harnish et al., "A Review of Polymer-Based Water Conditioners for Reduction of Handling-Related Injury", Reviews in Fish Biology and Fisheries 21, 2011, Netherlands, pp. 43-49.

Janak et al., "The Effects of Neutrally Buoyant, Externally Attached Transmitters on Swimming Performance and Predator Avoidance of Juvenile Chinook Salmon", Transmitters of the American Fisheries Society 141, 2012, United States, pp. 1424-1432.

Li et al., "Piezoelectric Materials used in Underwater Acoustic Transmitters", Sensor Letters vol. 10, 2012, United States, 65 pages.

MacGregor et al., "Recovery Strategy far the American Eel (Anguiiia reatrata) in Ontario". Ontario Recaveiy Strategy Series, Prepared for Ontario Ministry of Natural Resources, Peterboraagh, Ontario, 2013, Canada, 131 pages.

McGrath et al., "Studies of Upstream Migrant American Eels at the Moses-Saunders Power Dam on the St. Lawrence River near Massena, New York", American Fisheries Society Symposium 33, 2003, United States, pp. 153-166.

Mesa et al., "Survival and Growth of Juvenile Pacific Lampreys Tagged with Passive Integrated Transponders (PIT) in Freshwater and Seawater", Transactions of the American Fisheries Society 141, 2012, United States, pp. 1260-1268.

Mueller et al., "Tagging Juvenile Pacific Lamprey with Passive Integrated Transponders: Methodology, Short-Term Mortality, and Influence on Swimming Performance", North American Journal of Fisheries Management vol. 26, 2006, United States, pp. 361-366.

Normandeau, "Survey for Upsteam American Eel Passage at Holyoke Dam, Connecticut River, Massachusetts, 2006", Prepared for Holyoke Gas and Electric by Normandeau Associates, Inc., Apr. 26, 2007, United States, 68 pages.

Økland et al., "Recommendations on Size and Position of Surgically and Gastrically Electronic Tags in European Silver Eel", Animal Biotelemetry 1:6, 2013, United Kingdom, pp. 1-5.

Panther et al., "Influence of Incision Location on Transmitter Loss, Healing, Retention of Juvenile Chinook Salmon", Transactions of the American Fisheries Society 140, 2011, United States, pp. 1492-1503.

Summerfelt et al., "Anesthesia, Surgery, and Related Techniques", in Schreck, C.B., Moyle, P.B., (Eds.), Methods for Fish Biology, American Fisheries Society, 1990, United States, pp. 213-272.

Verdon et al., "Recruitment of American Eels in the Richelieu River and Lake Champlain: Provision of Upstream Passage as a Regional-Scale Solution to a Large-Scale Problem", American Fisheries Society Symposium 33, 2003, United States, pp. 125-138.

Walker et al., "Effects of a Novel Acoustic Transmitter on Swimming Performance Avoidance of Juvenile Chinook Salmon: Determination of a Size Threshold", Fisheries Research 176, 2016, Netherlands, pp. 48-54.

Ward et al., "A Laboratory Evaluation of Tagging-Related Mortality and Tag Loss in Juvenile Humpback Chub", North American Journal of Fisheries Management 35, 2015, United States, pp. 135-140.

(56) References Cited

OTHER PUBLICATIONS

Wuenschel et al., "Swimming Ability of Eels (Anguilla rostrata, Conger Oceanicus) at Estuarine Ingress: Contrasting Patterns of Cross-Shelf Transport?", Marine Biology 154, 2008, Germany, pp. 775-786.

Zale et al., "Effects of Surgically Implanted Transmitters Weights on Growth and Swimming Stamina of Small Adult Westslope Cutthroat Trout", Transactions of the American Fisheries Society vol. 134(3), 2005, United States, pp. 653-660.

\* cited by examiner

| Description | Designator | Manufacturer |
|---|---|---|
| CAP CER 10UF 10V 20% X5R 0402 | C10 | Samsung Electro-Mechanics America, Inc. |
| CAP CER 0.1UF 6.3V 20% X5R 01005 | C11, C12 | Samsung Electro-Mechanics America, Inc. |
| LED BLUE RECTANGLE SMD 0402 | D10 | Panasonic Electronic Components |
| CONN HEADER 6POS PIC PRGM INTF | J10 | MOLEX |
| RES SMD 33K OHM 5% 1/32W 01005 | R10 | Panasonic Electronic Components |
| MCU 8BIT 8K FLASH 14CSP | U10 | Microchip Technology |
| Seiko Instruments 200MA VOLT REG ULTRA LOW IQ | U11 | Seiko Semiconductors |
| OSC CMOS PROG 1.8V OE SMD | Y10 | EPSON |

| Manufacturer Part Number | Quantity | VALUE | | |
|---|---|---|---|---|
| CL05A106MP5NUNC | 1 | 10µF | 10 µF capacitor | |
| CL02A104MQ2NNNC | 2 | 0.1µF | 0.1 µF capacitor | |
| LNJ947W8CRA | 1 | | blue LED | |
| 22-05-2061 | 1 | | programming header | |
| ERJ-XGNJ333Y | 1 | 33k | 33K ohm resistor | |
| PIC16F1823T/CL | 1 | | microcenter | |
| S-1313D18-A4T1U3 | 1 | | voltage regulator | |
| SG-8003CG-PE8 | 1 | | oscillator | |

FIG. 11

SIGNAL TRANSMITTER AND METHODS FOR TRANSMITTING SIGNALS FROM ANIMALS

CROSS REFERENCE TO RELATED APPLICATION

This application claims priority to U.S. Provisional Patent Application Ser. No. 62/267,797 which was filed on Dec. 15, 2015, the entirety of which is incorporated by reference herein.

STATEMENT AS TO RIGHTS TO INVENTIONS MADE UNDER FEDERALLY-SPONSORED RESEARCH AND DEVELOPMENT

This invention was made with Government support under Contract DE-AC0576RL01830 awarded by the U.S. Department of Energy. The Government has certain rights in the invention.

TECHNICAL FIELD

The present disclosure relates to signal transmitters and methods for transmitting signals from animals. In particular embodiments, the transmitters can be injectable and/or provide radio frequency signals.

BACKGROUND

Transmitters have revolutionized biologists' understanding of both terrestrial and aquatic animal movements since they were first attached to animals about 50 years ago. Accurate information on fish movement, for example, is needed to understand the impacts of hydroelectric dams on fish migration and survival so that mitigation techniques can be applied to recover endangered populations (or to prevent endangerment in the first place). However, biologists are limited by the relatively large size of transmitters because of the potential to negatively impact and bias animal behavior. For example, the American Ornithologists' Union suggested that the transmitter weight should not exceed 5% of the body weight of birds. American Society of Mammologists recommend transmitter weight should be less than 5% of the bats' body weight. Miniature radio-frequency (RF) transmitters used for tracking small aquatic, airborne, or terrestrial animals/objects that may be injected are provided herein.

SUMMARY OF THE DISCLOSURE

Injectable transmitters are provided that can include a body with the body housing a power source and an oscillator, the injectable transmitter also including an antenna extending from the body, the body and antenna being of sufficient size to be injected through a 9 gauge needle.

Radio frequency transmitters are provided that can include a body extending from a nose to a tail with the body housing a power source and RF signal generator components. The power source of the transmitter can define at least a portion of the nose of the body. The transmitters can have an antenna extending from the tail.

Methods for attaching a radio frequency (RF) transmitter to an animal are provided. The methods can include providing an RF transmitter and providing an injection device having a needle of gauge of 9 or smaller; providing the RF transmitter into the injection device; and providing the RF transmitter through the 9 gauge or smaller needle and into the animal.

BRIEF DESCRIPTION OF THE FIGURES

FIG. 11 is a part list of components of a transmitter according to an embodiment of the disclosure.

DESCRIPTION

Figure 1:
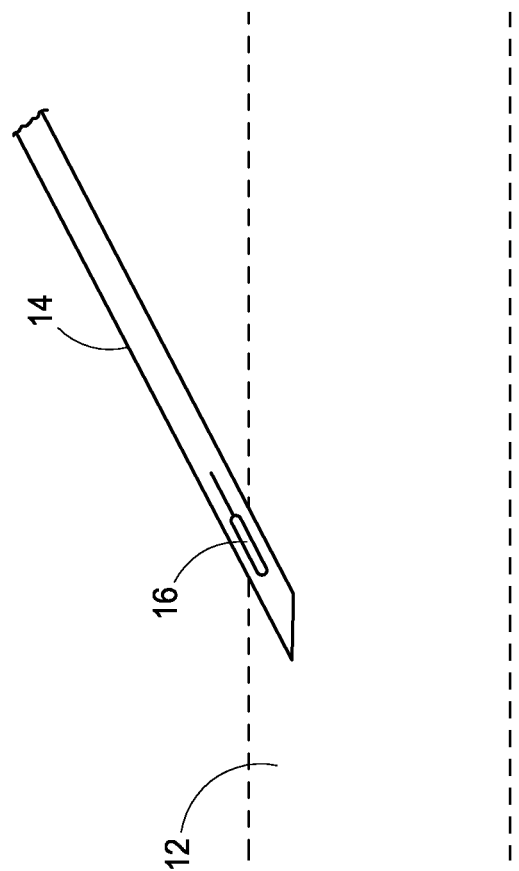
FIG. 1 is a depiction of implantation of a transmitter according to an embodiment of the disclosure.

This disclosure is submitted in furtherance of the constitutional purposes of the U.S. Patent Laws "to promote the progress of science and useful arts" (Article 1, Section 8).

To enhance the ability to study the survival of small fishes through hydroelectric dams, a smaller and more powerful radio-frequency (RF) transmitter, which can be injected into fish using a 9-gauge needle, is provided. Designs of two transmitters were developed: one that transmits coded signals and one that transmits un-coded signals. To accommodate different transmitter life requirements, each design can be configured to provide a high or low signal strength.

The coded transmitter is 2.95 mm diameter and 11.85 mm long, and weighs merely 160 mg. Depending on the ping rate (or PRI, pulse rate interval), the coded low-signal-strength transmitter has a projected service life of 11 days@2 s, 27 days@5 s and 52 days@10 s. By way of comparison, the smallest commercially available radio frequency transmitter for animals (NTQ-1, Lotek Wireless Inc., Newmarket, ON, Canada) has 6-58% lower operating lifetimes, despite being somewhat larger than the disclosed designs. The coded high-signal-strength transmitter has a comparable service life to the Lotek NTQ-1.

The un-coded transmitter is 2.95 mm diameter and 11.22 mm long, and weighs 152 mg. It provides even longer service life than the coded transmitter. Its low-signal-strength variant can last 15 days@2 s, 37 days@5 s and 69 days@10 s.

Definitive determination of a preferred surgical implantation method was complicated due to several factors in the bio-effects evaluation. However, at the end of the study (day 14), the Incision-Cath method had the lowest percentage of open wounds (4.2%), the smallest wound size (1.14 mm$^2$), and the lowest percentage of transmitter loss (10%), and is likely the best method for transmitter implantation based on this pilot evaluation. Although the injection method had the fastest implantation time, and may allow cost-savings for telemetry studies with large sample sizes of tagged fish, the percentage of dropped transmitters (47.5%) was the highest of any treatment.

Referring to FIG. 1, a method for attaching a radio frequency transmitter 16 through a needle 14 into an animal 12 is depicted. Transmitter 16 is as described herein and needle 14 has a gauge of 9 or less. As depicted, transmitter 16 can be injected into animal 12. This can be a subcutaneous injection if desired or more or less invasive injection. Animal 12 can be any ambulatory being including but not limited to fish for example.

The transmitter can have a cylindrical body with a diameter of 2.95 mm or less to be compatible with a 9-gauge needle, for example. The transmitter can be encapsulated in an epoxy resin for rigidity and the transmitter body can be coated with a 25-μm layer of Parylene-C to provide waterproofness and/or bio-compatibility.

Figure 2:
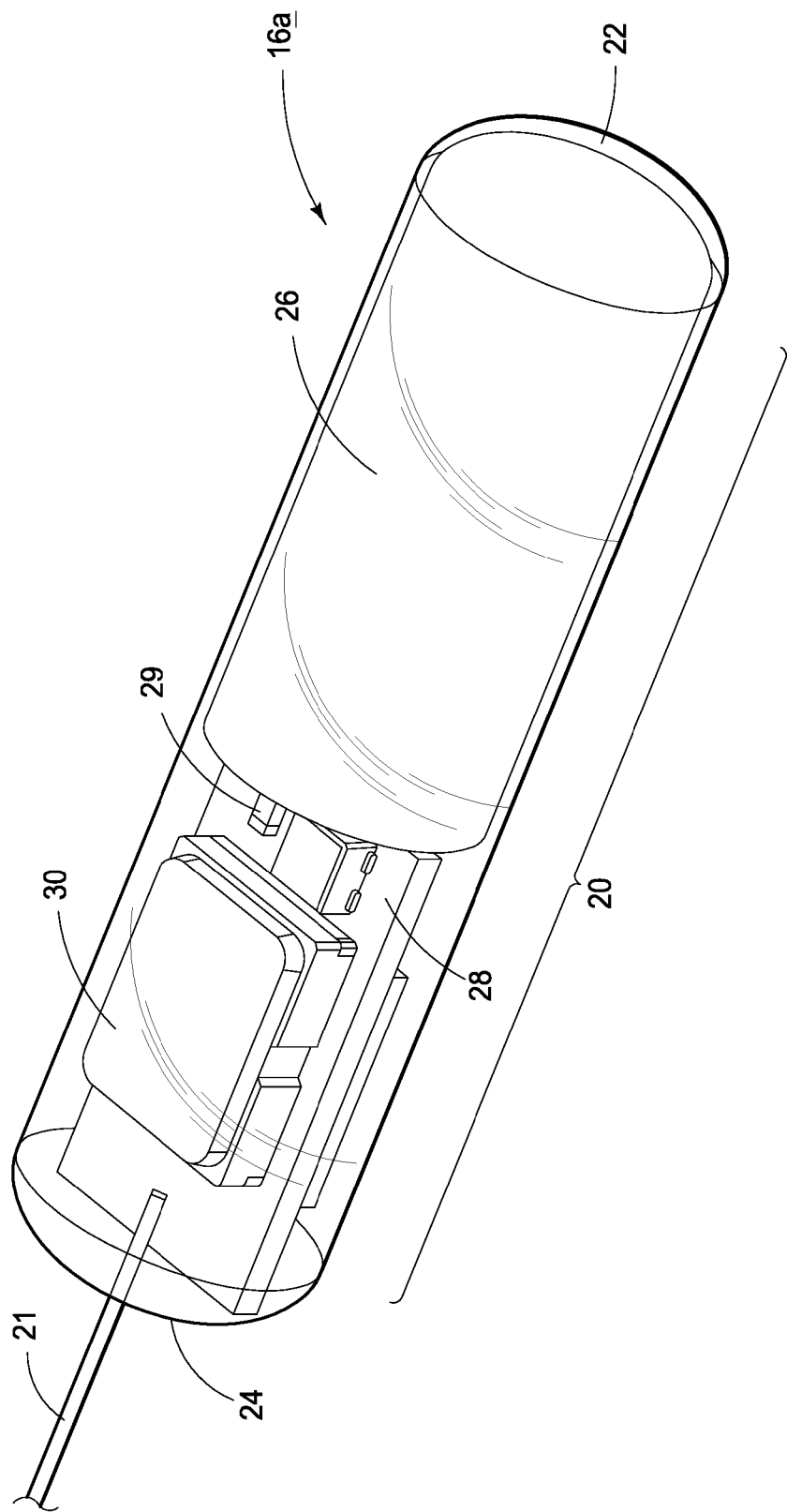
FIG. 2 is one perspective view of a transmitter according to an embodiment of the disclosure.

Referring next to FIG. 2, transmitter 16a is shown according to an embodiment of the disclosure. According to this embodiment, transmitter 16a includes a body 20 and an antenna 21. Body 20 can extend between a nose 22 and a tail 24. Preferably, injection of the transmitter proceeds nose first, for example. Transmitter 16a can include a power source 26 that can define at least a portion of the nose. This power source can be a battery such as that battery disclosed in U.S. patent application Ser. No. 14/014,035 filed Aug. 29, 2013, the entirety of which is incorporated by reference herein. Transmitter 16a can include RF signal generating components such as voltage regulator 28, capacitor 29 and oscillator 30.

Figure 3:
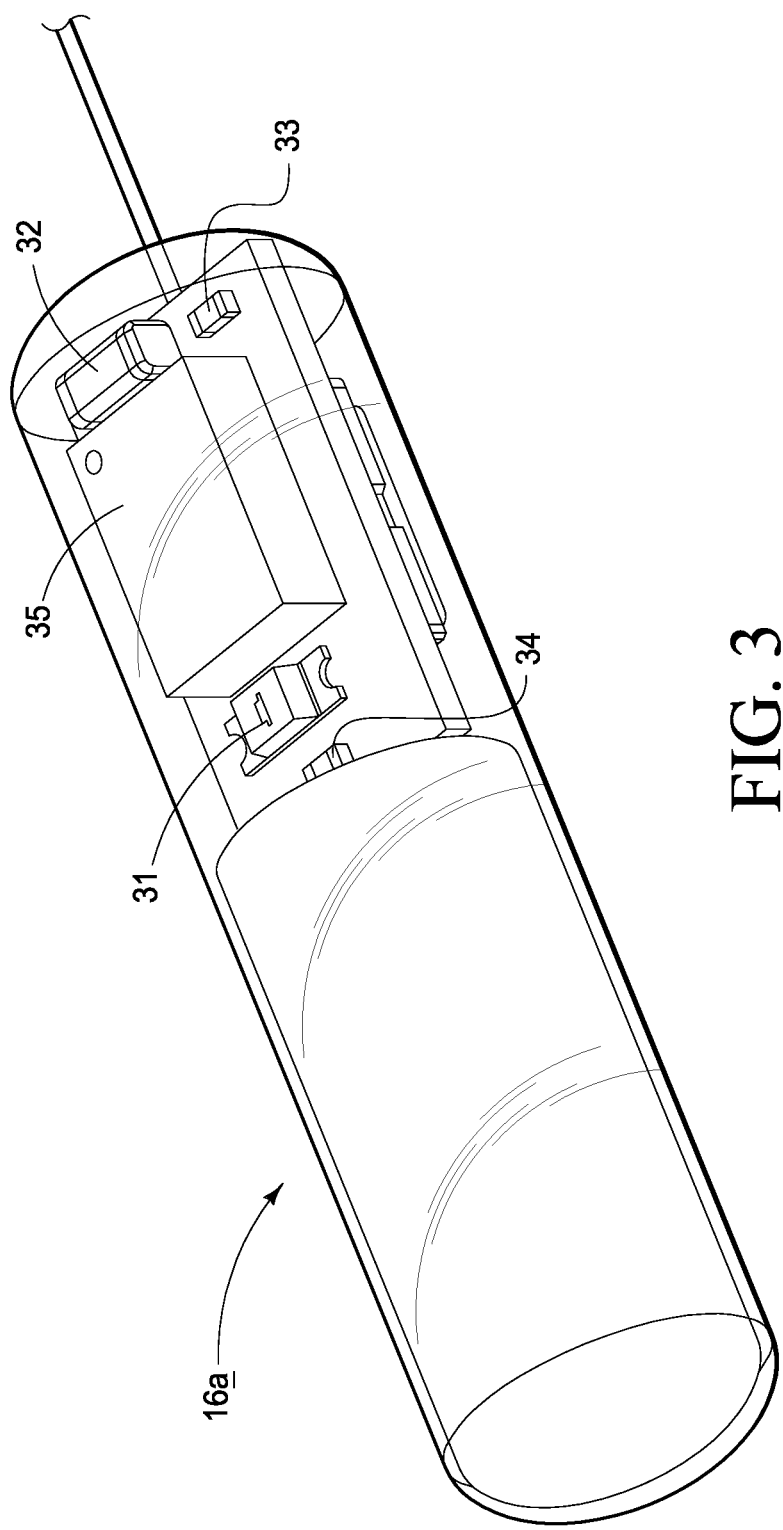
FIG. 3 is another perspective view of the transmitter of FIG. 2 according to embodiment of the disclosure.

Referring next to FIG. 3, according to another view of transmitter 16a, additional components are shown in operable alignment. For example, transmitter 16a can include LED 31 (blue), microcontroller 35, capacitor 32, resistor 33, and another capacitor 34.

Figure 4:
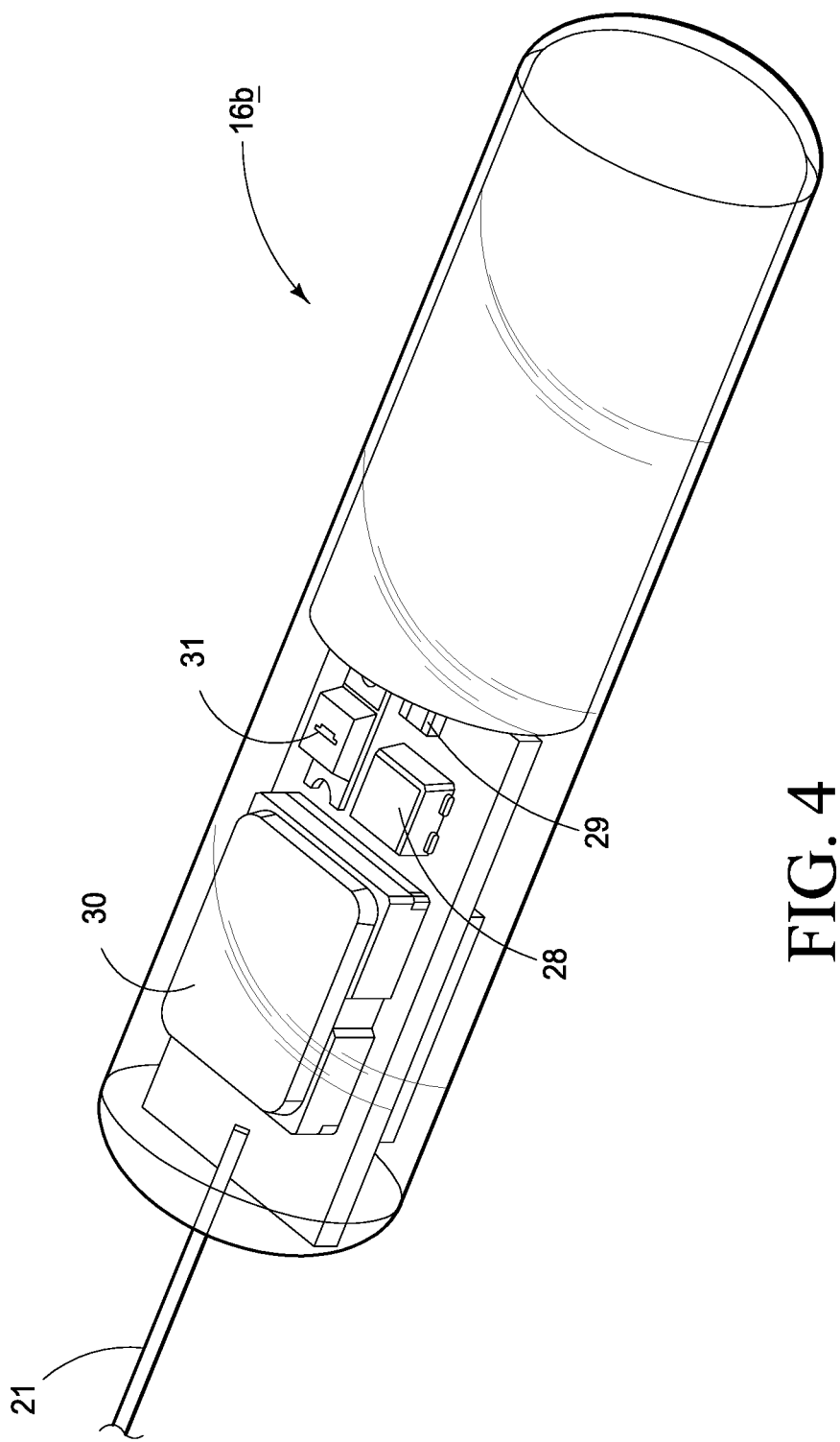
FIG. 4 is one perspective view of a transmitter according to another embodiment of the disclosure.

Other component configurations of the transmitters are contemplated. For example, transmitter 16b is shown in FIG. 4. Transmitter 16b can include LED 31 mounted next to oscillator 30, for example.

Figure 5:
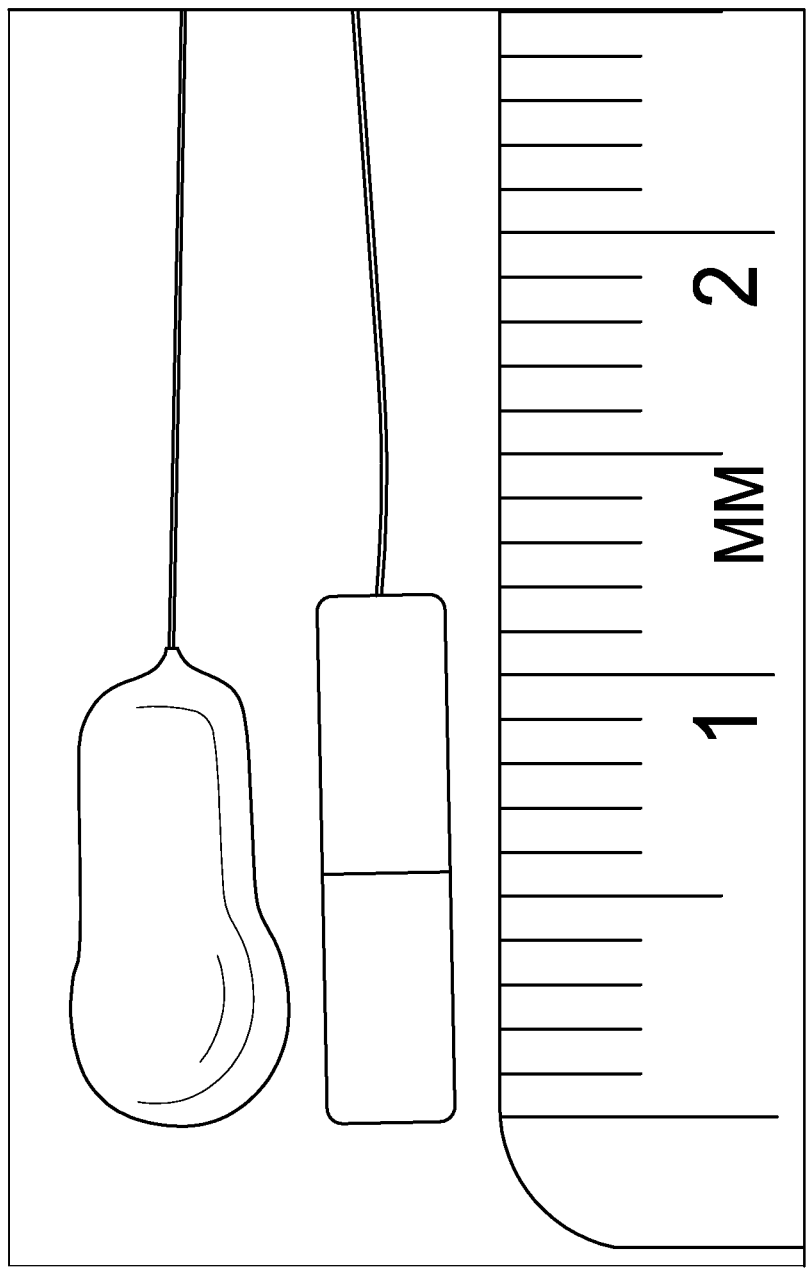
FIG. 5 is a depiction of a transmitter of the prior art and a transmitter of the present disclosure.

Referring next to FIG. 5, a transmitter of the present disclosure is pictured (bottom) side by side with the commercially available radio frequency transmitter referenced above (Lotek NTQ-1, top).

The transmitters can include three components: an antenna component for transmitting RF signals, a circuit board component containing the controlling circuitry, and a cylindrical micro-battery component that powers the transmitter. The antenna can be a Teflon PFA (perfluoroalkoxy)-coated stainless steel wire that has a diameter of 38.1 μm. The length of the antenna can be varied to achieve the desired resonance frequency of the transmitter (e.g., 17.8 cm=~164 MHz). To meet the transmitter life goal, the transmitter can use a Li/CF$_x$ micro-battery consisting of lithium metal anode and carbon fluoride cathode, which has a capacity of 6 mAh and is 6 mm long. Compared to the traditional silver oxide button-cell batteries, which are commonly used in small commercial radio transmitters, the Li/CF$_x$ batteries have the advantages of high energy and power density as well as high average operating voltage (3.1-3.4 volts), long shelf life and a wide operating temperature range.

To fabricate the prototype transmitter, the micro-battery can be first attached to the circuit board using a silver-filled epoxy such as the 8331 (MG Chemicals, Ontario, Canada). The antenna can be soldered to the circuit board. For encapsulation, this RF transmitter assembly can be coated with an insulating epoxy such as the EPO-TEK 301 epoxy (Epoxy Technology Inc., Billerica, Mass.) using a flexible mold, which can be made from flexible materials (e.g. silicone rubber). The mold can have cavities that define the shape of the transmitter. After the RF transmitter assembly is placed into the cavity, the insulating epoxy can be injected into the bottom of the cavity using a syringe with a small needle until the epoxy fills up the cavity. The mold may be left to stand overnight for the epoxy to cure. After removal from the mold, the transmitter may be gently sanded with sand paper and polished using a rotary polishing tool to eliminate any sharp edges or burrs. Finally, the RF transmitter can be coated with 25-μm thick Parylene-C to become waterproof and/or bio-compatible.

Two different designs (Option 1 and Option 2 hereinafter) of the injectable RF transmitter are provided as example implementations, but other implementations are contemplated. Option 1 transmits un-coded RF signals at a set ping rate, whereas Option 2 transmits coded RF signals.

A first embodiment (i.e. Option 1) can be 11.22 millimeters in length and weighs less than 152 milligrams.

A second embodiment (i.e. Option 2) can have an extra crystal to control the timing of RF signal so that it can generate coded RF signals. The second embodiment can be about 0.63 mm longer and 8 mg heavier than the first embodiment.

Figure 6:
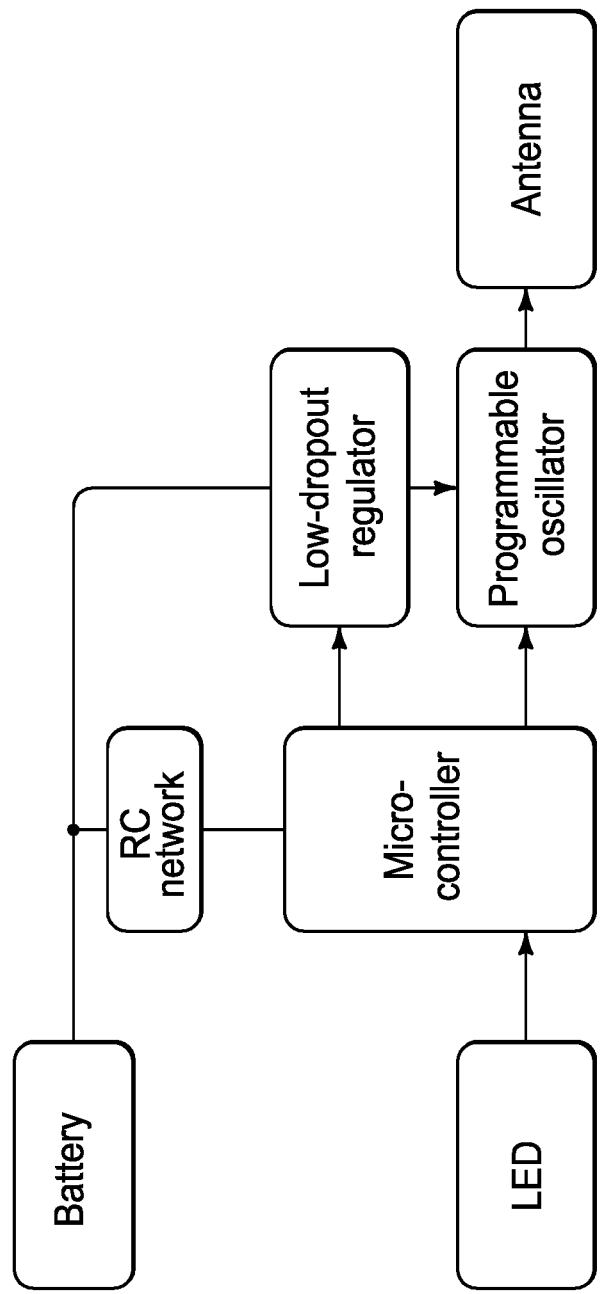
FIG. 6 is a block diagram depicting components of a transmitter according to an embodiment of the disclosure.

A block diagram of the first embodiment (i.e. Option 1) transmitter is shown in FIG. 6. This design includes a microcontroller, a resistor-capacitor (RC) network, a light emitting diode (LED), a low-dropout voltage (LDO) regulator and a programmable oscillator.

The microcontroller controls various circuits and functions within the injectable RF transmitter. It executes embedded firmware (source code) that defines its operation, which includes turning the programmable oscillator on and off to control the transmitted signal.

The RC circuit isolates the microcontroller from the voltage drop of the battery and keeps it from entering brownout state.

The LED provides an optical link for programming through a personal computer. This component is not used in the typical manner: rather than generating light when a voltage is applied across its terminals, the LED generates a voltage across its terminals when exposed to ultraviolet light. A configuration apparatus (not shown) may utilize a USB-to-TTL converter circuit and a second LED to convert serial commands from a personal computer to a coded series of "on" and "off" pulses of light, which then may be converted back into electrical signals by the first LED on the transmitter. This first LED is then coupled to one of the pins on the microcontroller. The above mechanism provides a small yet effective way to activate the microcontroller and specify operating parameters such as the PRI.

The LDO regulator outputs a fixed voltage at 1.8 V to power the programmable oscillator, because the typical input voltage of the programmable oscillator ranges from 1.6 V to 2.2 V.

The programmable oscillator generates a symmetric square wave signal. The Fourier series of a square wave is $$\text{square}(t) = \frac{4}{\pi} \sum_{n=1}^{\infty} \frac{\sin(nt)}{n} = \frac{4}{\pi} \left( \frac{\sin(t)}{1} + \frac{\sin(3t)}{3} + \frac{\sin(5t)}{5} + \ldots \right)$$

A square wave only contains odd harmonics and the amplitude decreases in inverse portion to harmonic order n. For this application, the FCC frequency range can be 164~168 MHz. The programmable oscillator can be programed to 54.667~56.000 MHz for high-strength signals to generate a sine wave at 164~168 MHz using the 3rd harmonic. This option consumes a current of 2.7 mA. The programmable oscillator can alternatively be programed to 32.8~33.6 MHz for low-strength signals using the 5th harmonic. This option consumes a current of 2.1 mA. The duration of the un-coded RF signal can be set to about 16 ms using the internal clock of the microcontroller.

Figure 7:
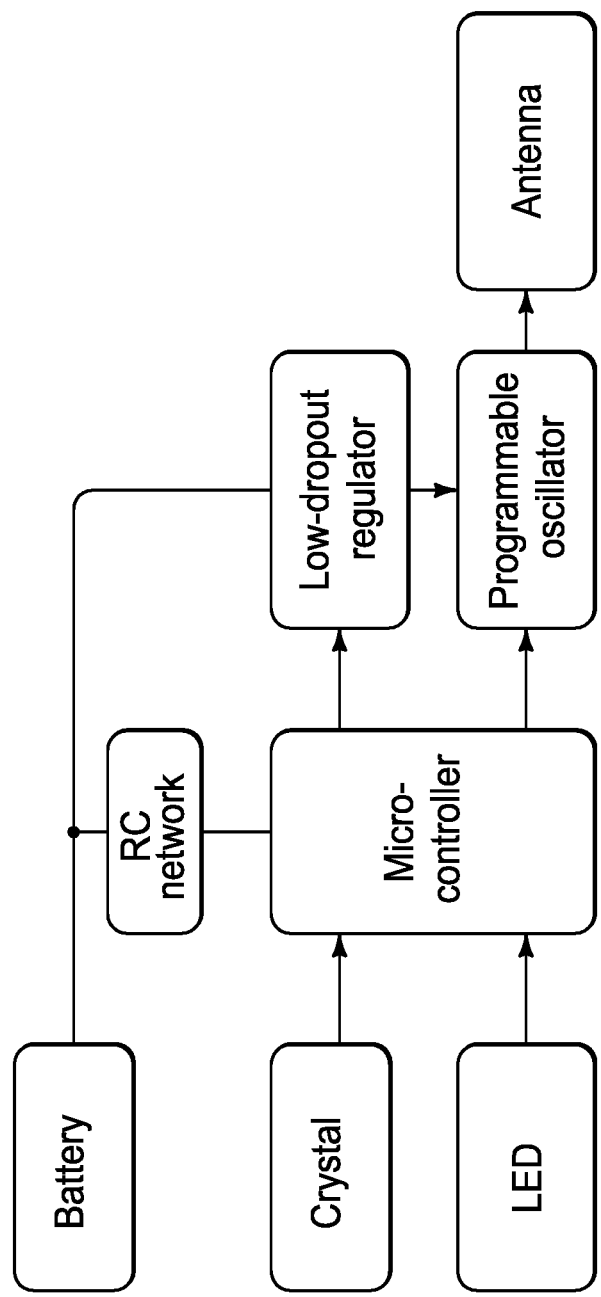
FIG. 7 is a block diagram depicting component of a transmitter according to another embodiment of the disclosure.

A block diagram of the second embodiment (i.e. Option 2) transmitter is shown in FIG. 7. This design includes a microcontroller that uses an external clock signal from an added quartz crystal to accurately control the timing of the oscillator. This mechanism allows the transmitter to generate coded RF signals. The microcontroller can also use the crystal to calibrate its internal clock. To allow multiple transmitters broadcasting on the same frequency, a pattern of pulses unique to each individual transmitter can be used.

Figure 8:
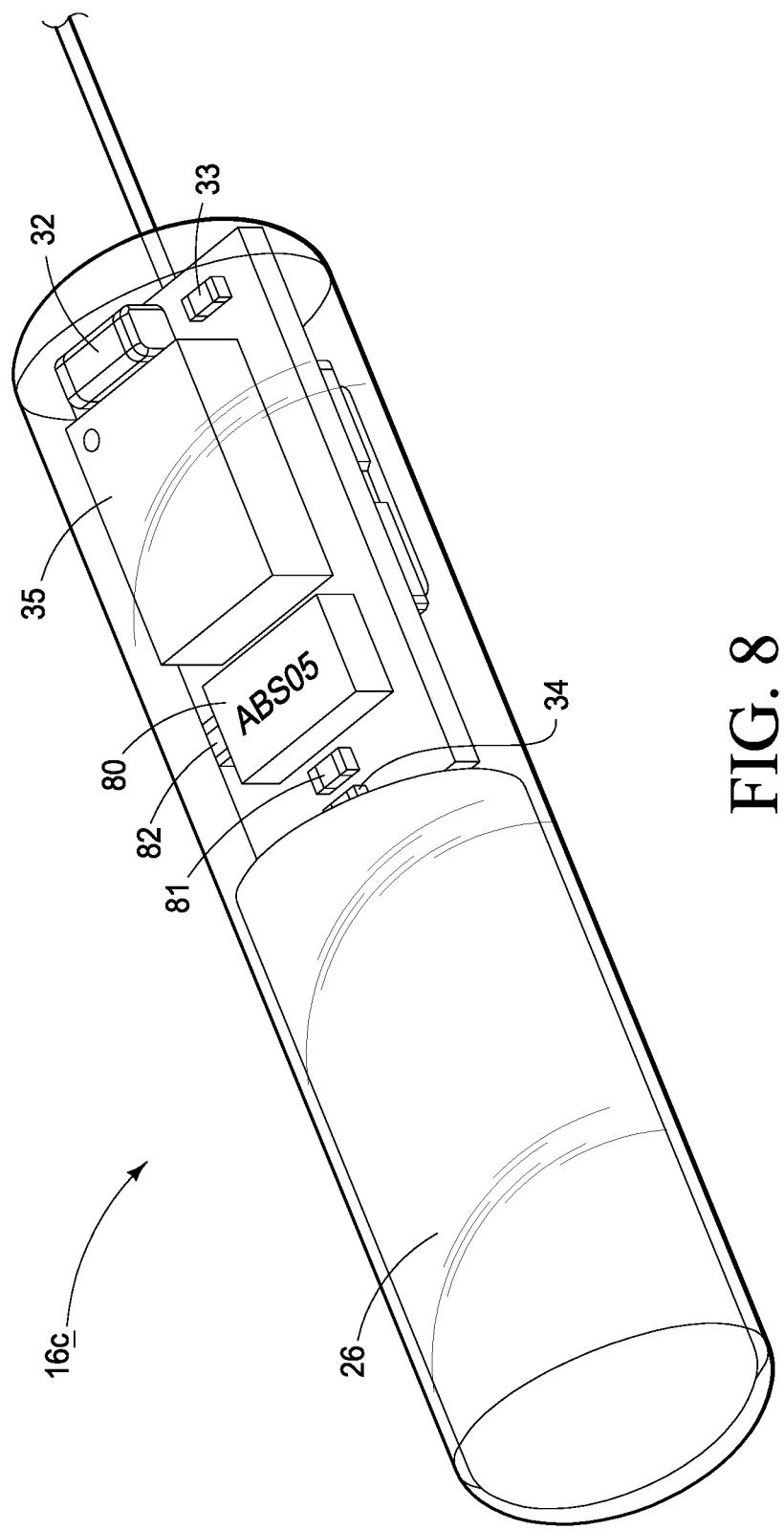
FIG. 8 is one perspective view of a transmitter according to an embodiment of the disclosure.
Figure 9:
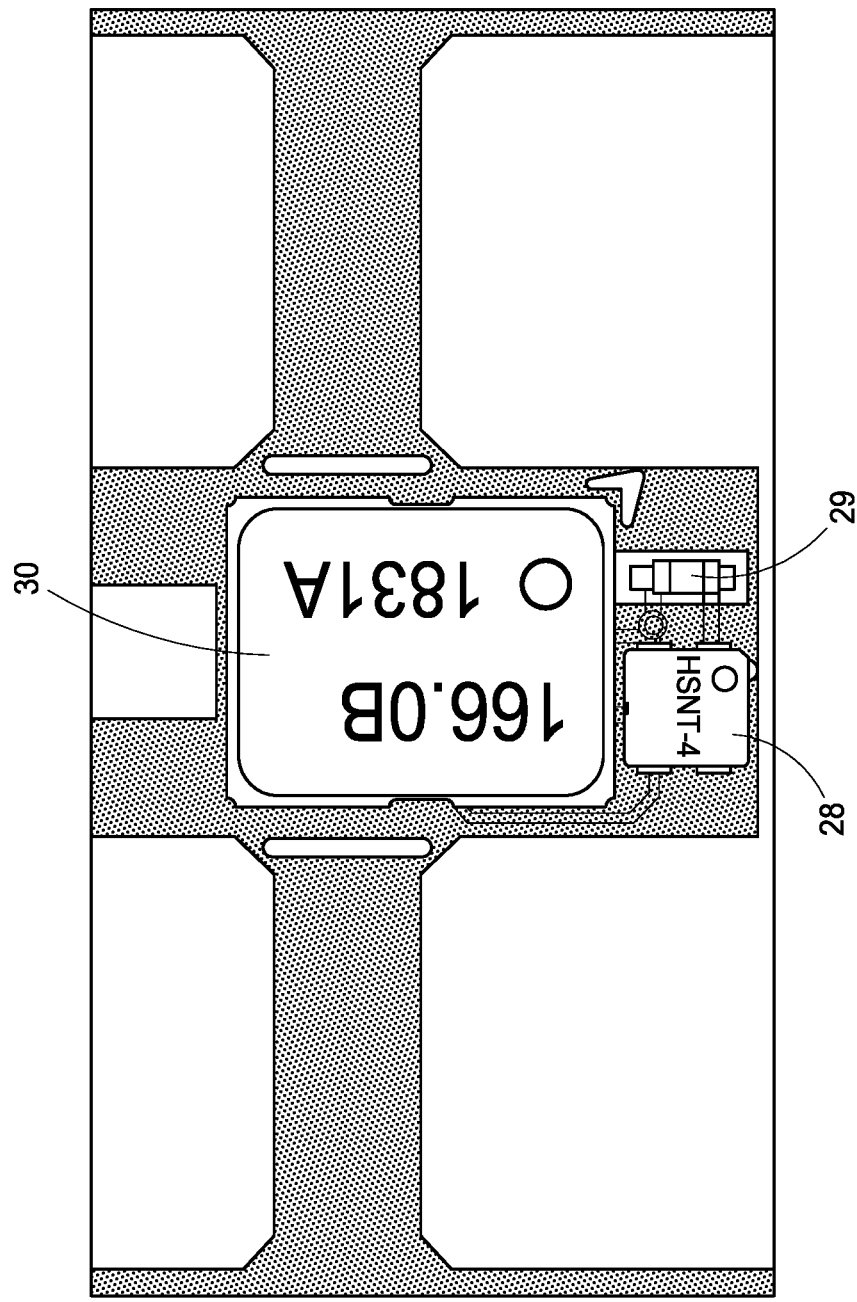
FIG. 9 is a depiction of a component of a transmitter according to an embodiment of the disclosure.
Figure 10:
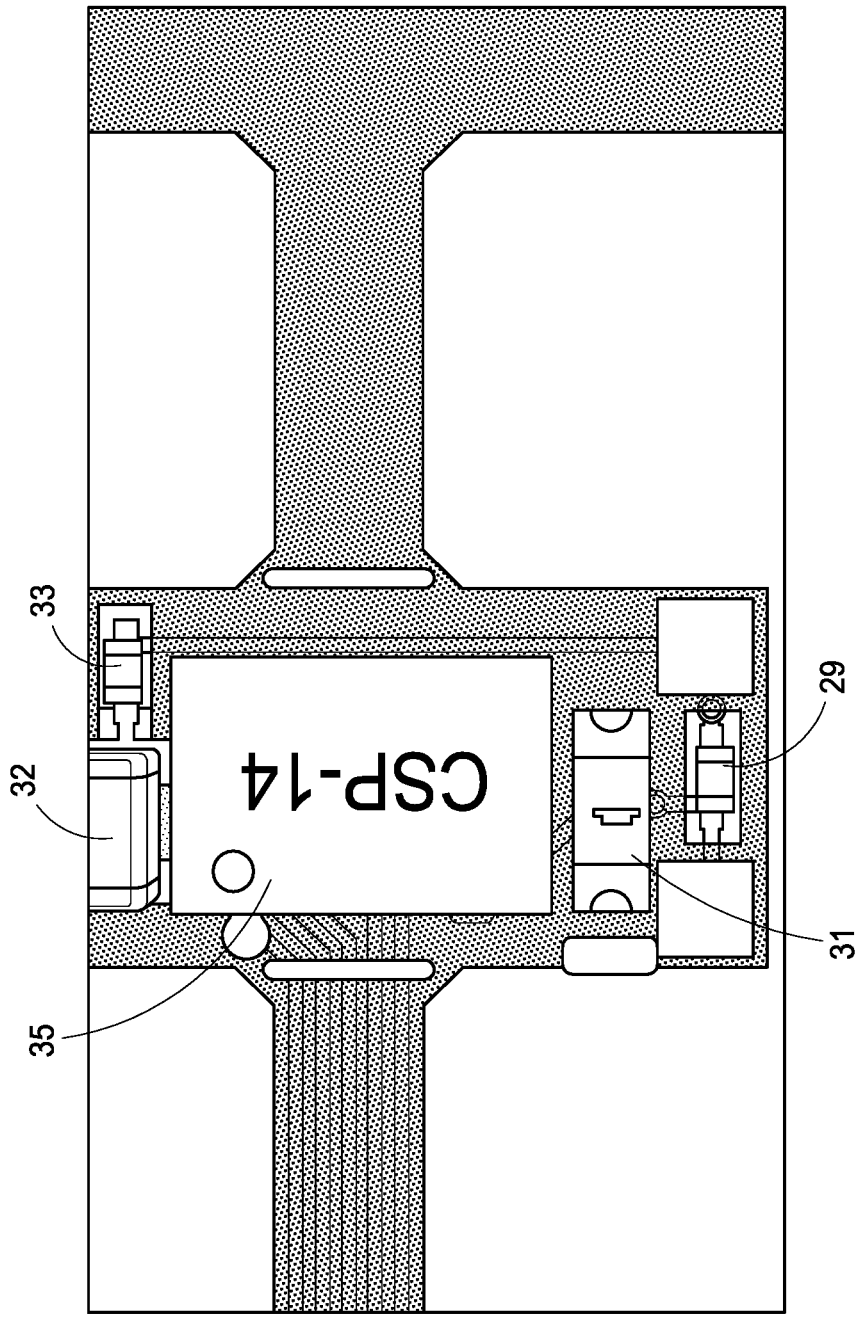
FIG. 10 is a depiction of another component of a transmitter according to an embodiment of the disclosure.

Referring next to FIG. 8, a depiction of the second embodiment (i.e. Option 2) transmitter 16c that includes crystal 80 and additional capacitors 81 and 82 is shown. Referring to FIG. 9, a more detailed view of the oscillator 30, voltage regulator 28 and capacitor 29 are shown associated with a circuit board of the transmitter. Referring to FIG. 10, additional components of the same circuit board, but opposing side can include microcontroller 35, capacitor 32, resistor 33, LED 31, and capacitor 29.

Figure 12A:
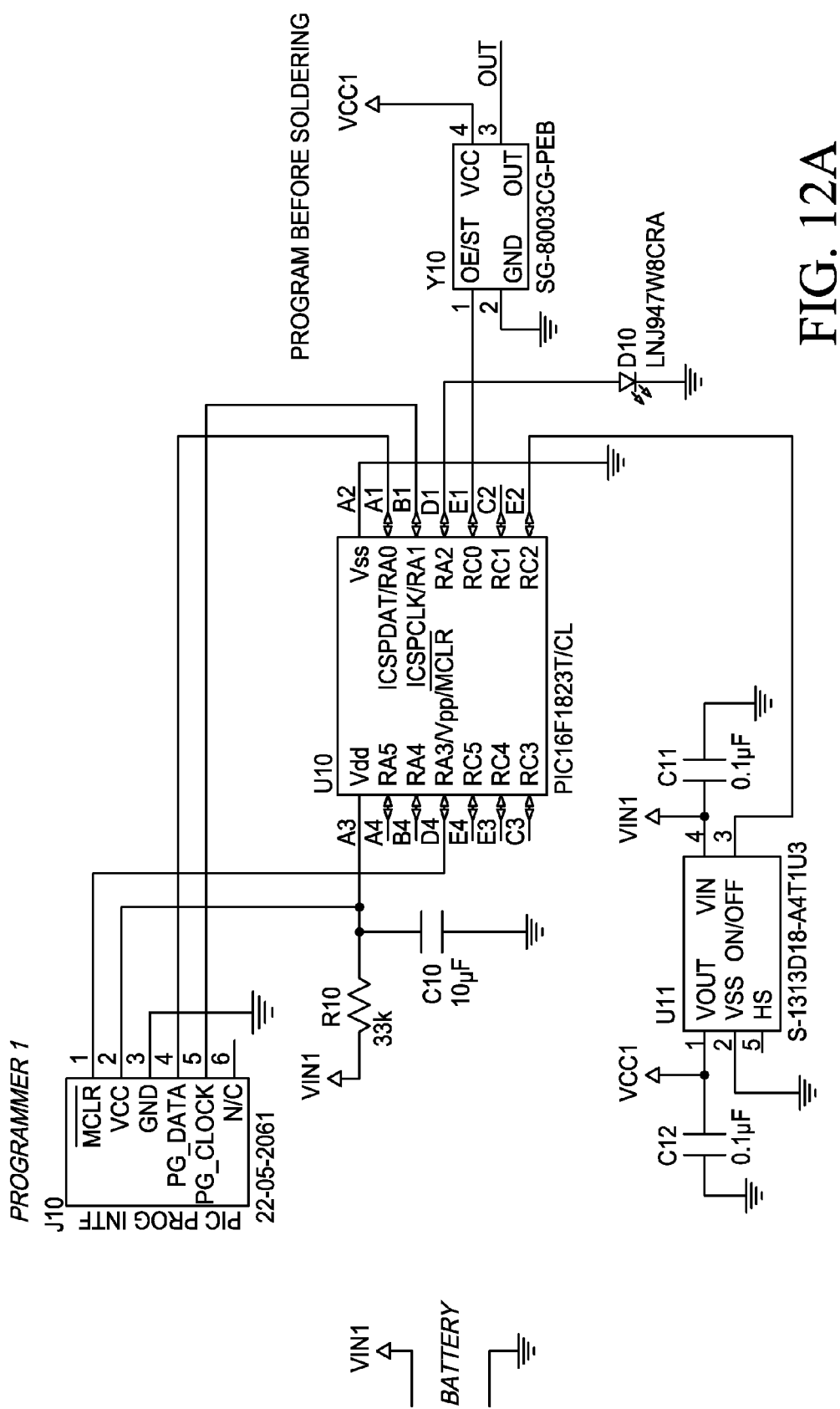
FIGS. 12A and 12B are circuit diagrams of component configurations of a transmitter without a crystal and with a crystal according to two embodiments of the disclosure.
Figure 12B:
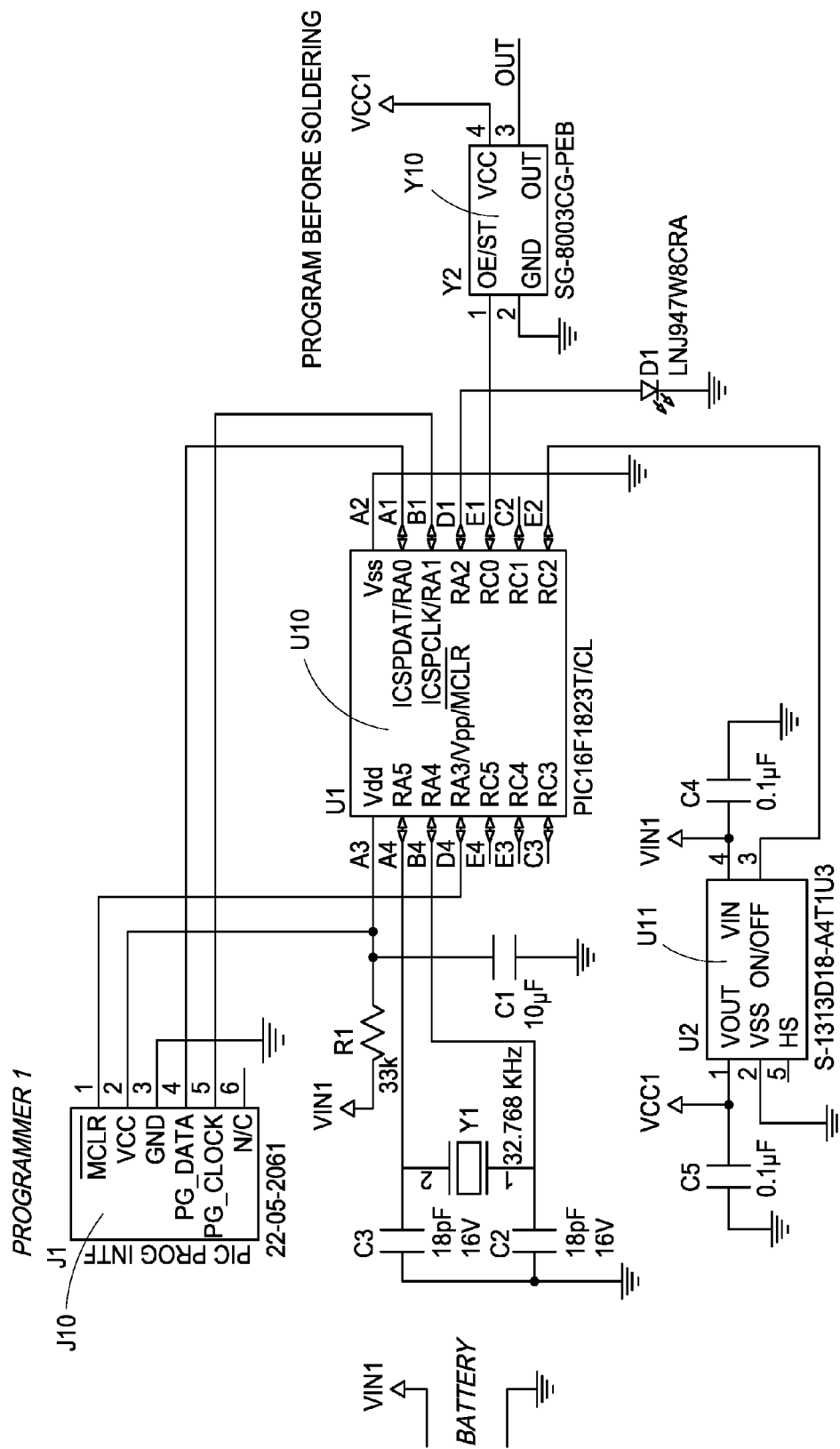

Referring next to FIG. 11 a general electronic component parts list is provided that can be arranged in accordance with the circuit diagram of FIGS. 12A and 12B. FIG. 12A is representative of the first embodiment (i.e. Option 1) transmitter and FIG. 12B is representative of the second embodiment (i.e. Option 2) transmitter.

Signal output can be compared between the two prototype transmitters and the smallest commercially available transmitter. The test can be performed outdoors to minimize the effects of electromagnetic noise and other signals. The test transmitters can be placed about 10-cm apart and parallel to each other and the signal receiver (Sigma Eight Orion receiver with an omnidirectional whip antenna) was located about 6 m away. The receiver antenna was arranged perpendicular to the transmitter antennas. All transmitters and receiver/antenna remained in the same place during the test.

Hatchery-reared spring Chinook salmon (*Oncorhynchus tshawytscha*) were used for all bio-effects experiments. After hatching, the juveniles were held in cold water until July 2015, when they were slowly acclimated to a water temperature of 12° C. to allow them to grow to an appropriate size for juvenile salmonid radio transmitter implantation (i.e., >95 mm). For 2 months prior to tagging and for the duration of this study, fish remained at 12° C. (±2° C.). Food was restricted for 24 hours prior to and 24 hours following implantation. On the day of implantation, fish ranged from 103-153 mm (mean=129.9 mm) in fork length (FL) and weighed 10.9-36.8 g (mean=23.6 g). All tools were disinfected (by ultraviolet light for surgical blade) or sterilized (by autoclave for stainless steel needles and catheters) prior to use. The 9-gauge needles were new on the day of tagging. After first use with the injection treatment, they were autoclaved and still very sharp for the 9 ga-needle with catheter treatment.

Since implantation time was an important variable in this study, rather than randomize the treatment order throughout the tagging day, each treatment was completed in a block. Using this design, the tagger was able to standardize the technique of implantation and to become efficient with the process. Thus, theoretically, this tagging order produced the fastest implantation times for each of the three treatments with the radio transmitter tested. In addition, the efficiency is representative of the process in which fish would be tagged in a field study where only one technique is used.

"Dummy" transmitters of the second embodiment described above that were equal in dimensions and mass to the functioning transmitter (i.e., the larger prototype suitable for coded transmitters) were used for the bioeffects study. It had dimensions of 2.95 mm×2.95 mm×11.85 mm and contained within its volume an 8.4 mm long passive integrated transponder (PIT) tag (HPT8, Biomark). This PIT tag permitted unique identification of the dummy transmitter if it were shed during the post-tagging holding period. Currently in a radio telemetry study in the Willamette River basin, PIT tags also are being implanted alongside radio transmitters in smolts for PIT tag detection downstream of Foster Dam. Therefore, for this laboratory study, a 12.5 mm PIT tag (HPT12, Biomark) was implanted along with the dummy radio transmitter. Unfortunately, the presence of 2 PIT tags in a single fish makes neither tag detectable due to their proximity. However, every tag dropped could be immediately identifiable. At the completion of this study, fish were again identifiable during necropsy by scanning each tag individually.

On Sep. 15, 2015, fish were netted from a 4-ft diameter circular rearing tank and placed in a 20-L bucket filled with aerated river water. One at a time, fish were placed in an anesthetic bucket with a dosage of 80 mg/L Tricaine Methanesulfonate for ~3 min or after a complete loss of equilibrium. Fish were then immediately weighed, measured, and tag codes assigned. The tagger then implanted the anesthetized fish using one of three treatment methods: surgical incision with catheter (aka Incision-Cath), 9-gauge needle injection (aka Injection), and 9-gauge needle with catheter (aka 9 GA-Cath). For both of the catheter treatments, fish were placed on a wet, grooved, surgery pad (coated with PolyAqua, a water conditioner) for stabilization and their gills were irrigated with fresh water through rubber tubing from a gravity-fed tank. For the injection treatment, fish were stabilized in the tagger's hand. Detailed descriptions of the treatments are explained below.

Method 1: Surgical incision with catheter (Incision-Cath)—With the fish facing ventral side up, a surgical blade was used to make ~3-mm incision on the linea alba (midventral line). The incision was made ~5 mm anterior of the pelvic girdle. To place the antenna through the body wall, a 19-gauge stainless steel needle shielded with a 16-gauge stainless steel catheter was carefully guided through the body cavity posterior to the pelvic girdle. Then, the 19-ga needle was unshielded to make a hole through the body wall. The needle remained in the fish while the catheter was pulled back out through the incision. The end of the transmitter antenna was then threaded through the tubing of the needle. Both the needle and antenna were pulled posteriorly until the needle was out of the fish and the antenna was threaded through the body wall. Next, the PIT tag was inserted into the peritoneal cavity. Lastly, the transmitter body was guided into the peritoneal cavity as the antenna was gently guided posteriorly. Unlike most field radio tagging studies, a suture was not used to close the incision. Recent laboratory studies using an injectable acoustic transmitter of similar size showed 100% long-term transmitter retention with a ~3 mm incision in salmon as small as 80 mm in length (unpublished data).

Method 2: 9-gauge needle injection (Injection)—To prepare the tags for injection, first the transmitter was loaded into the 9-ga needle by inserting the rounded transmitter end through the hub end of the needle. If the dummy transmitter body was slightly too wide to be inserted through the hub, then the slower loading method was used. The slower method consisted of threading a short section of the transmitter antenna through the 16-ga catheter and guiding it through the pointed end of the needle. The antenna could not be threaded directly through the needle and hub (without the aid of the catheter) because the end of the antenna would catch on an edge inside the needle and the antenna could become kinked. After loading the transmitter into the needle, the needle hub was screwed onto an implanter (Biomark MK10 implanter). Modifications to the implanter included removal of the spring and notching the tip of the implanter to permit the antenna wire to hang outside the implanter body. Next, the PIT tag was loaded into the pointed end of the needle and this completed the preparation phase of tagging. The fish was then held ventral side up with its head facing away from the tagger. Using a bevel-down technique similar to that described by Cook et al. (2014), the needle was used to puncture the body wall ~3-5 mm anterior of the pelvic girdle and ~5 mm off the linea alba, on the left side of the fish. The needle was inserted to a shallow depth to create a hole just large enough for the transmitter. With a plunge of the implanter, the PIT tag, followed by the dummy transmitter, were injected anteriorly into the peritoneal cavity. Pressure was applied to the wound with the left thumb to ensure the transmitter was retained while the needle was drawn out of the fish and the antenna moved forward through the implanter and needle.

Method 3: 9-gauge needle with catheter (9 GA-Cath)—Before the fish was placed on the surgery pad, the 19-ga needle, shielded with the 16-ga catheter, was inserted into the hub end of the 9-ga needle (the implanter was not used for this technique). With the fish facing ventral side up on the pad, the 9-ga needle was used to make a small opening (~3 mm; equal to the width of the transmitter) near the distal end of the right pectoral fin ~3-5 mm from the linea alba. Then, the shielded 19-ga needle was carefully guided through the body cavity posterior to the pelvic girdle. The 19-ga needle was unshielded to make a hole through the body wall. The needle remained in the fish while the catheter and 9-ga needle were pulled away from the fish. The end of the transmitter antenna was then threaded through the tubing of the needle. Both the needle and antenna were pulled posteriorly until the needle was out of the fish and the antenna was threaded through the body wall. Next, the PIT tag was inserted into the peritoneal cavity. Lastly, the transmitter body was guided into the peritoneal cavity as the antenna was gently guided posteriorly.

After tagging, images were taken of the implantation wounds: two wounds each for fish implanted by methods 1 or 3, and one wound each for fish implanted by method 2. Fish were placed ventral-side up on a pad and they were supplied with water through rubber tubing throughout the imaging process. They were returned quickly to a recovery bucket supplied with aerated river water. Once ~10 fish were recovered, they were transferred to the holding tank where they resided for the duration of the study.

At 14 days post-surgery, fish were euthanized in 250 mg/L MS-222. Images were taken of the wounds as the external fish assessment was completed. Wounds were examined for openness, redness/inflammation, and ulceration. It was also noted whether the antenna was still present outside of the fish. The fish was then necropsied to determine radio transmitter and PIT tag retention and to identify the fish (by scanning each tag). Evaluation of tag encapsulation and/or adhesions was also completed at this time. Measurements of the wound area were made post-hoc.

All analyses were done with JMP version 7 (The SAS Institute, Cary, N.C.) at an alpha=0.05. Assumptions of equal variances and normality were verified prior to parametric statistical procedures.

The signal strengths of both high and low-signal-strength variants of the second embodiment prototype were tested to compare with that of the Lotek NTQ-2. Both of the prototype transmitters were found to be consistently about 10 dB stronger (−76 and −77 dBm, respectively for the high and low-signal-strength designs) than the Lotek NTQ-2's (−88 dBm).

Transmitters of the present disclosure also have similar or better service life compared to Lotek NTQ-1 and NTQ-2. The energy consumption of the transmitters was calculated by $$E_{trans} = V * I * T$$

V is the battery voltage in volts; we choose an average value of 2.5 Volts in the service life calculations. I is the average current consumed during transmission and T is the duration of each transmission.

For transmitters of the first embodiment, the duration is 16 ms for each RF signal transmission. For low signal strength, current I is 2.1 mA and the energy consumption is 84 µJ. For high signal strength, current I is 2.7 mA and the energy consumption is 105 µJ.

For transmitters of the second embodiment, the total pulse duration is about 22 ms for each RF signal transmission. For low signal strength, current I is 2.1 mA, the energy consumption is 115.5 µJ. For high signal strength, current I is 2.7 mA, the energy consumption is 148.5 µJ.

The service life calculation in Table 1 was based on the battery capacity 6 mAh, constant static current 0.5 uA that flows through the transmitter circuit, PRI.

The total energy of battery in transmitters can be calculated by $$E_{battery} = V * C * 3600 / 1000$$

V is the battery voltage in volts, C is the battery capacity in mAh, the number 3600 is used to convert hours to seconds and 1000 is used to convert mAh to Ah.

The total energy of battery can also be calculated by $$E_{battery} = E_{total\_trans} + E_s$$

$E_{total\_trans}$ is the total energy consumed by transmissions throughout the service life of the transmitter and $E_s$ is the energy consumed by the static current that constantly flows through the transmitter circuit.

Therefore, the total energy of battery can be expressed as:

$$E_{battery} = E_{trans} * n + V * I_s * T = E_{trans} * \frac{T}{PRI} + V * I_s * T = \left(\frac{E_{trans}}{PRI} + V * I_s\right) * T$$

$E_{trans}$ is energy consumption of each transmission, n is total number of transmission throughout the service life. $I_s$ is constant static current 0.5 µA that flows through the transmitter circuit. PRI is the pulse rate interval (ping rate) and T is the service life in seconds.

Because the total number of transmission n can be calculated by $$n = \frac{T}{PRI}$$

The service life in days can be calculated as $$T = \frac{E_{battery}}{\frac{E_{trans}}{PRI} + V * I_s} = \frac{V * C * 3600/1000}{\frac{E_{trans}}{PRI} + V * I_s} \bigg/ 3600 \bigg/ 24 = \frac{V * C/1000/24}{\frac{E_{trans}}{PRI} + V * I_s}$$

It is worth noting that the actual service life of the transmitter is usually slightly longer than the projected values based on this equation, because the battery voltage gradually decreases at a slow rate as it discharges, which consequently causes the $E_{trans}$ decreases over time.

Table 1 provides the size, weight, and calculated service life comparisons between the Lotek transmitters and the example transmitters.

TABLE 1

The comparison of Lotek, example transmitters

| Transmitter | Size w × h × l (mm) | Weight (air) (mg) | Calculated Life (days) | | | |
|---|---|---|---|---|---|---|
| | | | 2 s PRI | 5 s PRI | 10 s PRI | 60 s PRI |
| Lotek | | | | | | |
| NTQ-1 | 5*3*10 | 260 | 10 | 21 | 33 | 59 |
| NTQ-2 | 5*3*10 | 310 | 16 | 33 | 52 | 94 |
| 1st Embodiment | | | | | | |
| Low signal strength | 2.95*11.22 | 152 | 15 | 37 | 69 | 245 |
| High signal strength | 2.95*11.22 | 152 | 12 | 30 | 56 | 217 |
| 2nd Embodiment | | | | | | |
| Low signal strength | 2.95*11.85 | 160 | 11 | 27 | 52 | 206 |
| High signal strength | 2.95*11.85 | 160 | 9 | 21 | 41 | 176 |

The actual service life of the first embodiment transmitter was tested at a 3 s PRI (Table 2). The test results are consistent with the projected value obtained using the equation described above.

TABLE 2

The prototype RF transmitter life testing results

| 1st Embodiment (3 s PRI) Transmitter | Calculated Life (days) | Measured Life (days) |
|---|---|---|
| Low-signal-strength Transmitter (test sample 1) | 23 | 30 |
| Low-signal-strength Transmitter (test sample 2) | 23 | 24 |

Figure 13:
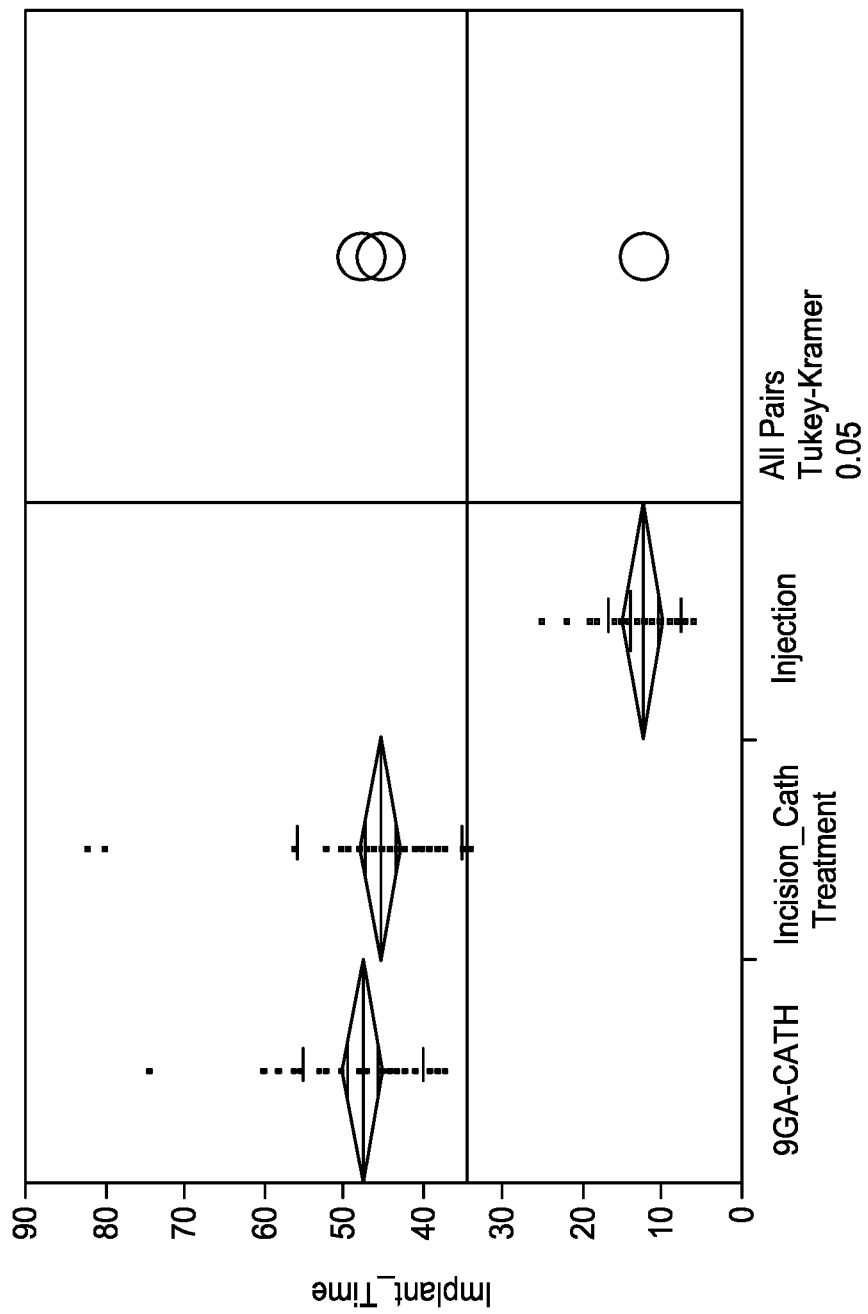
FIGS. 13-19 are graphical representations of animal wound data acquired when implanting transmitters of the present disclosure according to methods of the present disclosure.

No mortalities occurred throughout the 14-day duration of the experiment; however, surgery time and surgery maladies differed between the three surgical techniques/treatments. Implantation time significantly differed between the 3 treatment types (P<0.0001) with the Injection treatment having the fastest time (mean=12 s, SE=1.3 s) and the 9 GA-Cath and Incision-Cath treatments having times of 48 s (SE=1.3) and 45 s (SE=1.3), respectively (FIG. 13). Preparation time for the Injection treatment was also measured for 15 surgeries, and when combined with surgery time, resulted in an average total surgery time of 29 seconds (SE=3.14).

FIG. 13 depicts Implantation time (seconds) of the 3 surgical implantation treatments. The horizontal line in the green diamond represents the mean, upper and lower bounds of the diamond represent $25^{th}$ and $75^{th}$ percentiles, and blue horizontal lines indicates $5^{th}$ and $95^{th}$ percentiles. Means comparisons are also shown in the right panel using the Tukey-Kramer HSD test.

Figure 14:
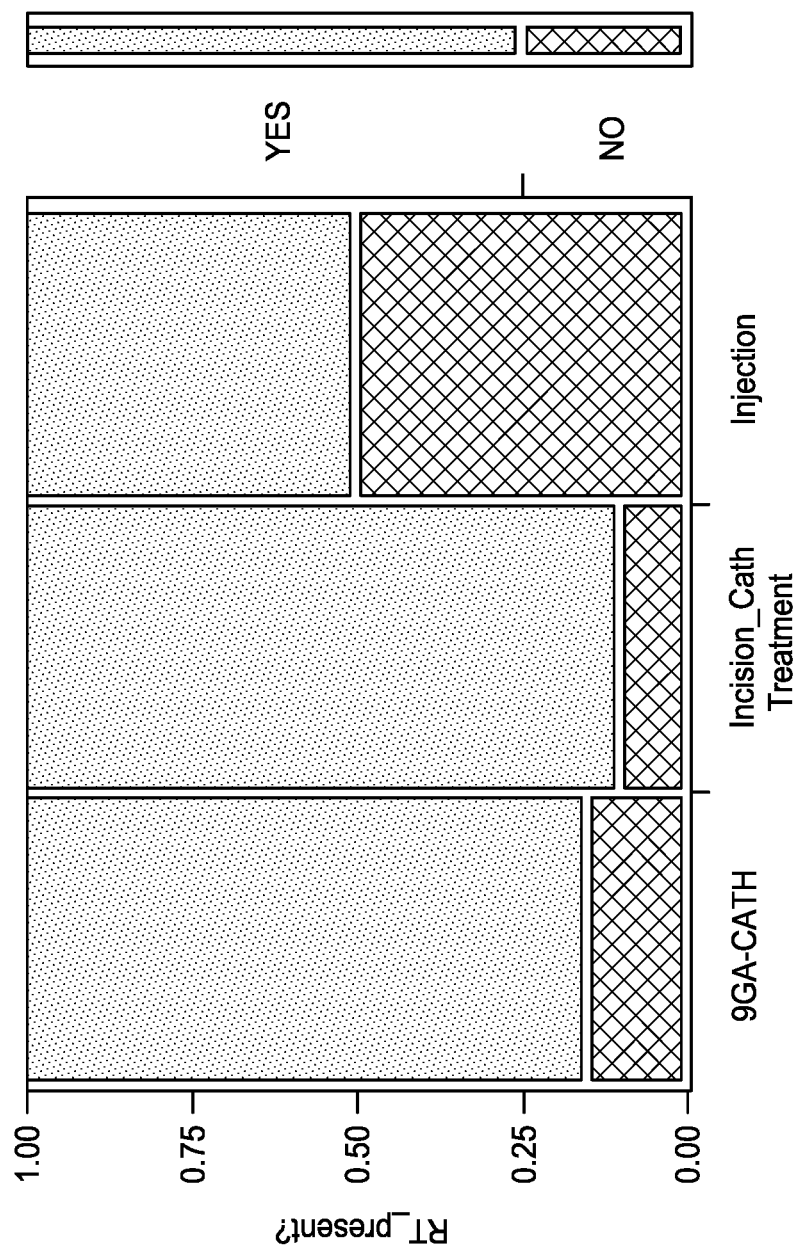

The percentage of dropped tags and dropped antennas differed significantly between treatments (tags, P=0.0002; antennas, P=0.001). Injection treatment fish lost the most tags (47.5%) whereas 9 GA-Cath (15%) and Incision-Cath (10%) lost fewer tags (FIG. 14). Injection fish also lost the most antennas (65%) compared to either 9 GA-Cath (27.5%) or Incision-Cath (40%). The difference in percentages between lost antennas and tags was due to the antennas falling off of the tag bodies and the tag bodies remaining inside the fish.

FIG. 14 depicts percentages of fish that retained (dotted "Yes") or lost (cross-hatched, "No") their RF transmitters through the final day of the study (Day 14).

Figure 15:
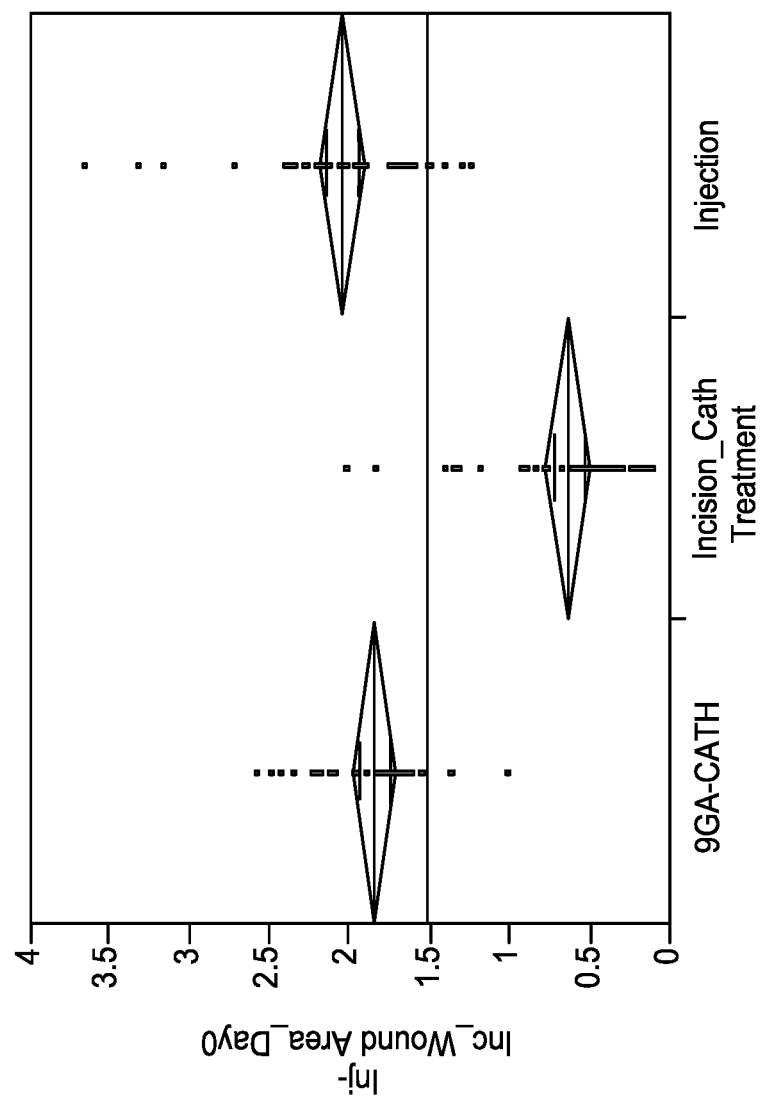
Figure 16:
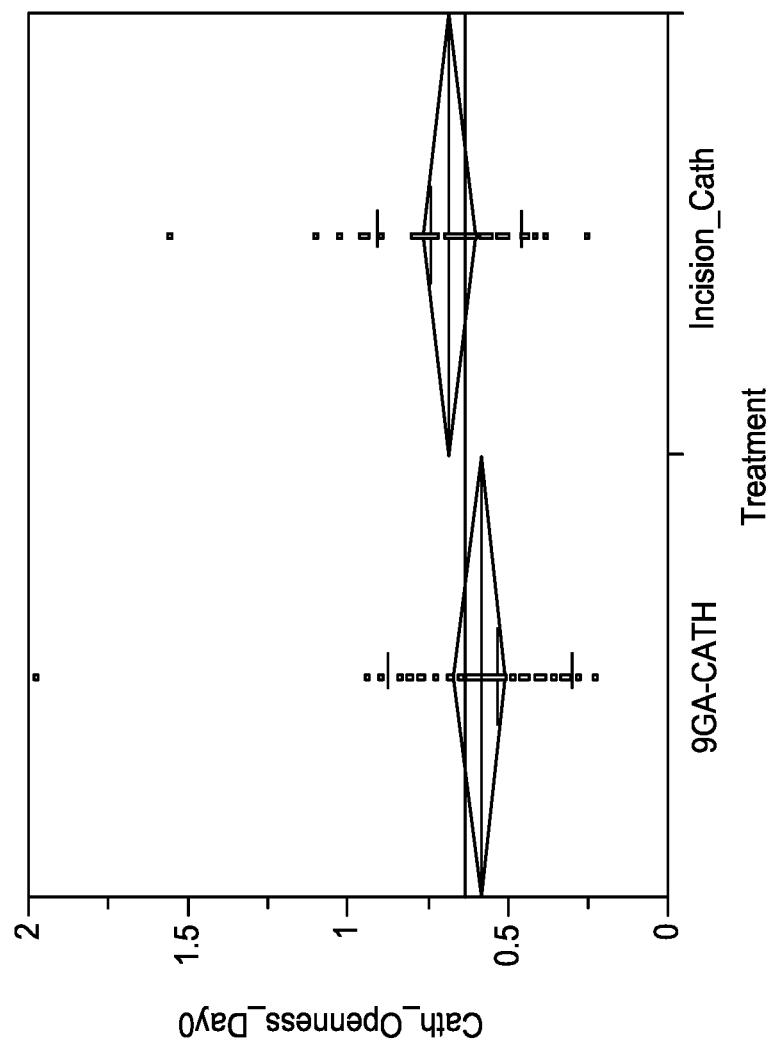

Wound area at Day 0 (day of tagging) for the Injection-Incision site (i.e., hole made that tag body was inserted through) was significantly different between treatments (P<0.0001; FIG. 15). The Injection treatment wound (mean=2.04 mm², SE=0.07) and 9 GA-Cath wound (mean=1.84 mm², SE=0.07) were relatively large and statistically similar whereas the Incision-Cath wound was significantly smaller (mean=0.63 mm²; Tukey HSD). Catheter site wound area did not differ between the 9 GA-Cath and Incision-Cath treatments (P=0.0885; FIG. 16). Specifically comparing the wound area of the antenna-exit holes for each treatment (i.e., same as injection site for Injection treatment), the Injection treatment was significantly larger than either the 9 GA-Cath or Incision-Cath wound made by the catheter, which likely played a role in whether fish retained or lost their transmitters.

FIG. 15 depicts a comparison of the wound area of the injection-incision site at day 0. The horizontal line in the green diamond represents the mean, upper and lower bounds of the diamond represent $25^{th}$ and $75^{th}$ percentiles, and blue horizontal lines indicates $5^{th}$ and $95^{th}$ percentiles.

FIG. 16 depicts a comparison of the wound area of the catheter (Cath) site at day 0. The horizontal line in the green diamond represents the mean, upper and lower bounds of the diamond represent $25^{th}$ and $75^{th}$ percentiles, and blue horizontal lines indicates $5^{th}$ and $95^{th}$ percentiles.

Figure 17:
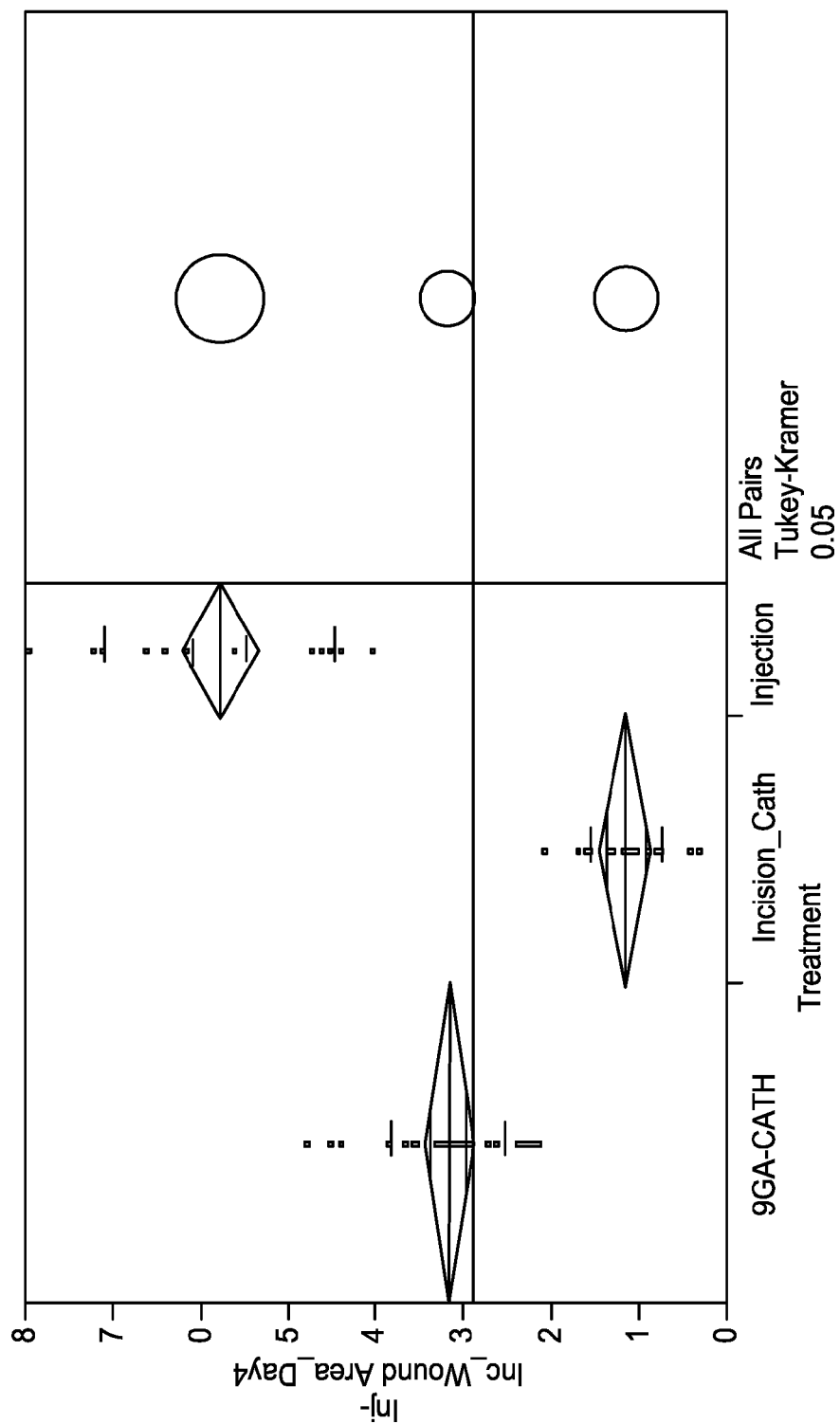

Wound area on Day 14 (end of study) was significantly different among treatment groups (P<0.0001; FIG. 17) with Injection fish having the largest wound area (5.77 mm²), 9 GA-Cath having an intermediate wound area (3.17 mm²), and Incision-Cath having the smallest wound area (1.14 mm²). However, it's important to note that fish that lost their tags or antennas were not included in these results because of inherent bias that losing a tag/antenna would have had on wound healing; thus, this analysis (and Figure) only include fish that retained their transmitter and antenna. Similar to Day 0, the wound area of the catheter site did not differ between 9 GA-Cath and Incision-Cath treatments (P=0.5592, FIG. 18).

FIG. 17 depicts a comparison of the wound area of the injection-incision (Inj-Inc) site at day 14 (end of study) for each of the 3 surgical treatments. The horizontal line in the green diamond represents the mean, upper and lower bounds of the diamond represent $25^{th}$ and $75^{th}$ percentiles, and blue horizontal lines indicates $5^{th}$ and $95^{th}$ percentiles. Tukey-Kramer HSD comparisons are included for reference.

Figure 18:
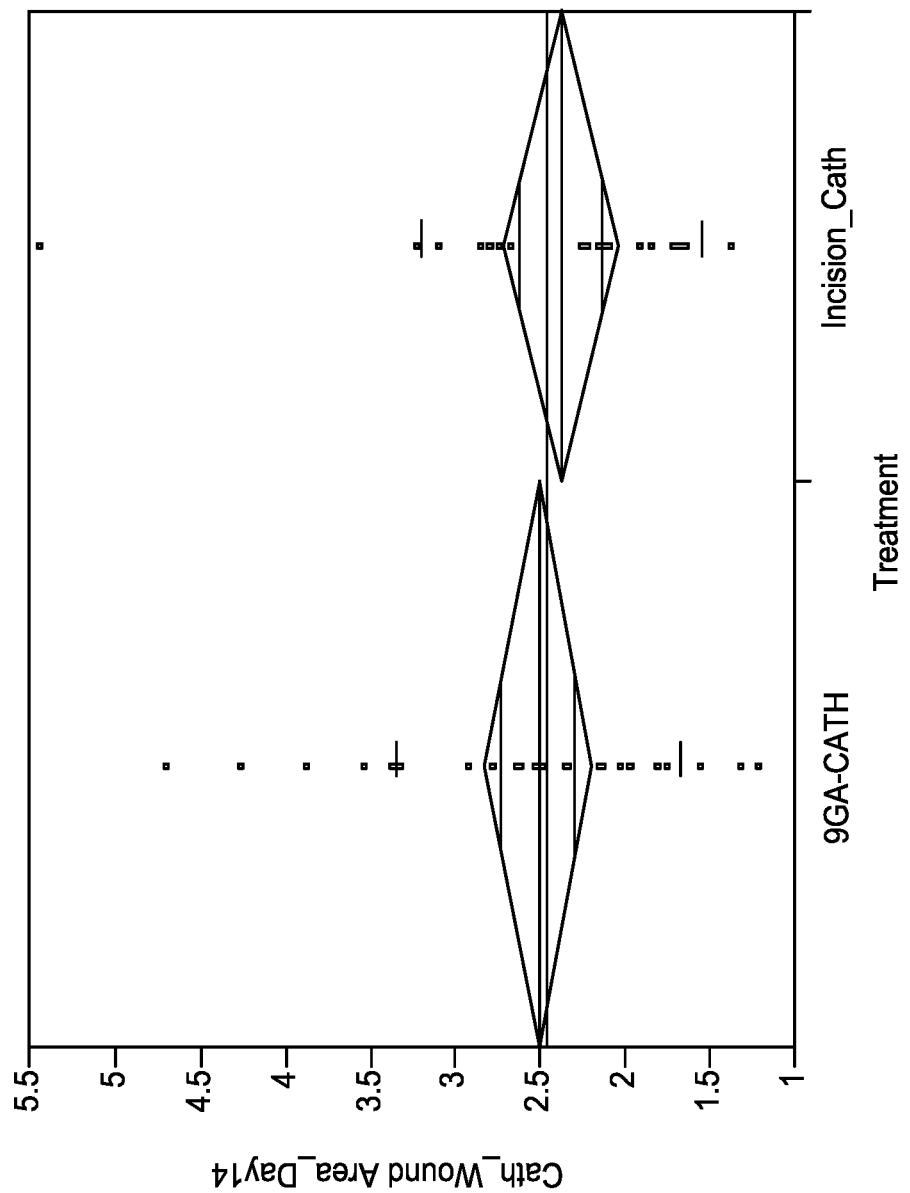

FIG. 18 depicts a comparison of the wound area of the catheter (Cath) site at day 14. The horizontal line in the green diamond represents the mean, upper and lower bounds of the diamond represent $25^{th}$ and $75^{th}$ percentiles, and blue horizontal lines indicates $5^{th}$ and $95^{th}$ percentiles.

Predicting dropped transmitters. Using a stepwise multivariate modeling procedure, tag loss was significantly related to the treatment method (P<0.0001) as well as fish fork length (P=0.0168). However, the predictability of the final model was relatively weak ($r^2$=0.1837) with treatment contributing most to the model's prediction power ($r^2$=0.1391). Original predictor variables included treatment, fish fork length, inj-inc wound area at day 0, and catheter wound area at day 0.

Of the variables measured on the day 14 necropsy, only wound openness was significantly different among treatments (P<0.0001; Figure). All Injection treatment fish (N=13) had open injection wounds (i.e., unhealed with visible opening to internal organs) on day 14 whereas 24.1% (7 of 29) of the 9 GA-Cath treatment and 4.2% (1 of 24) of the Incision-Cath fish had open injection wounds.

No significant differences were found between catheter wound openness of the two catheter treatments (P=0.8916), redness/inflammation (P=0.3916), tag encapsulation (P=0.4931), or tag adhesion (P=0.2548; Table 3). No ulcerations were present on any necropsied fish.

Figure 19:
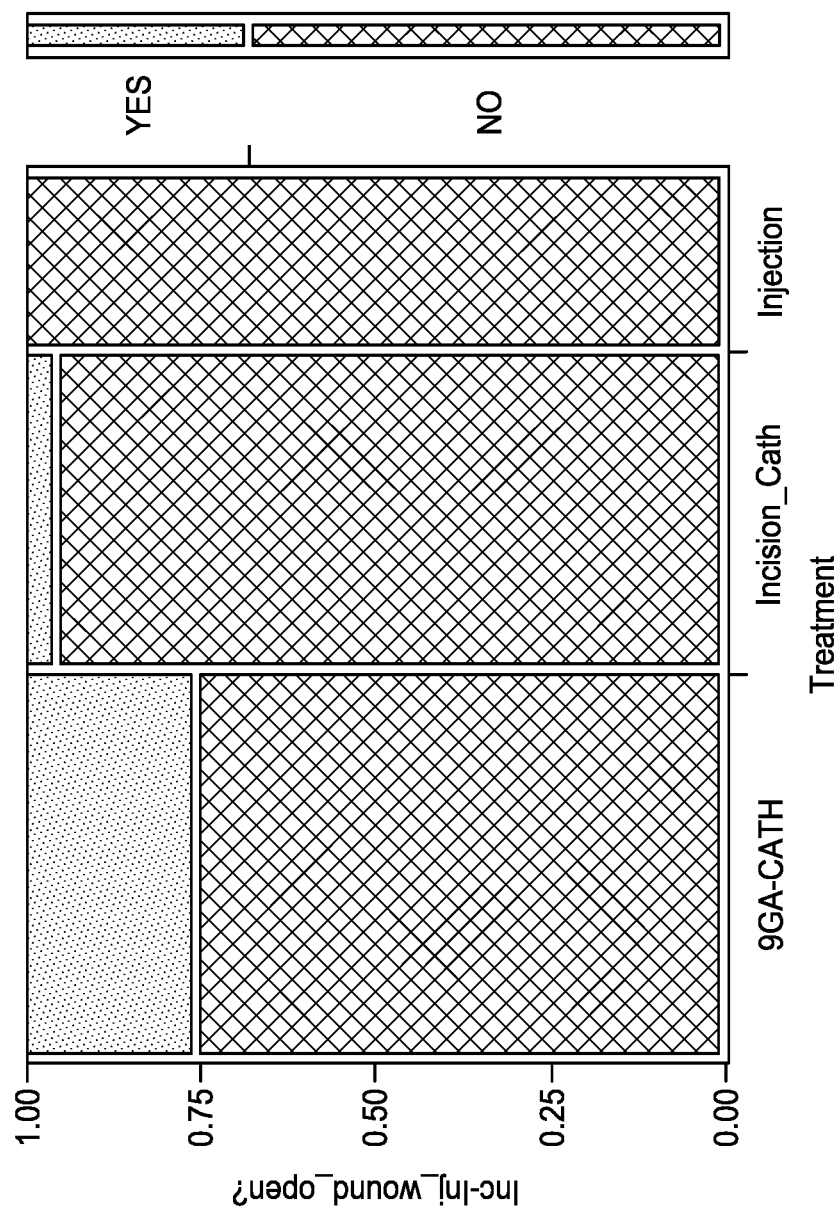

FIG. 19 depicts percentage of fish, by surgical treatment, with open Incision-Injection (Inc-Inj) wounds (dotted, "Yes") or closed wounds (cross-hatched, "No") during day 14 necropsies.

GA-Cath, and Incision-Cath treatments lost 17.5%, 12.5%, and 30% of their antennas, respectively, while tag bodies remained inside study fish. However, because fish from all treatments were located within the same tank during the 14 day observation period, we assume that all treatments had equal probability of having their antenna tangled and despite this, there were differences in tag loss with the Injection technique having greatest tag loss (47.5%) and the 9 GA-Cath (15%) and Incision-Cath (10%) methods having lower loss. Thus, we presume that tag loss was related more to the size of the open wound—the Injection technique had the largest wounds on both day 0 (2.04 mm2) and day 14 (5.77 mm2)—rather than due to the tangling of antennas alone.

Surgical implantation time is approximately the time that a fish is "out of water" during the surgical procedure; either on a surgical pad or held in the tagger's hand. The out of water time for the Injection treatment was faster than the 2 catheter techniques and would likely have beneficial effects with respect to fish health and survival. However, researchers should be cautious when relating the time savings of the Injection technique to budget/cost savings because the additional preparation time required to load the tags in the implanter needle ranged from 5-50 s (i.e. total load+implant time=13-59 s; mean=29 seconds, SE=3.14). Otherwise, if the tagger did not load the needle themselves, budgets would likely require an extra person tasked with loading tags for the entire tagging day. Alternatively, small modifications could be made to the transmitter or 9-gauge needle/implanter to keep loading times to ~5 s, thereby potentially improving the cost-savings estimates.

The pilot laboratory evaluation using the prototype injectable radio transmitter has provided an array of ideas on methods to improve and refine the transmitter design and implantation techniques. Qualitative improvements to the transmitter design based on the laboratory evaluation include creating a smoother antenna coating, using a different antenna material, and standardizing the tag body size. A

TABLE 3

Percentages of necropsy maladies (variable) by surgical treatment groups and wound locations.

| Variable | Treatment/Wound | | | | | P |
|---|---|---|---|---|---|---|
| | Injection | 9 GA-Cath/tag | 9 GA-Cath/cath | Inc-Cath/tag | Inc-Cath/cath | |
| Catheter wound open | NA | NA | 3.5% (1 of 29) | NA | 4.2% (1 of 24) | 0.8916 |
| Redness/inflammation present | 15.4% (2 of 13) | 3.5% (1 of 29) | 10.3% (3 of 29) | 4.2% (1 of 24) | 8.3% (2 of 240 | 0.3916 |
| Tag encapsulation | 30.8% (4 of 13) | 51.7% (15 of 29) | NA | 37.5% (9 of 24) | NA | 0.4931 |
| Tag adhesion | 7.7% (1 of 13) | 0% (0 of 29) | NA | 4.2% (1 of 24) | NA | 0.2548 |

Definitive determination of a preferred surgical implantation method was complicated due to several factors in the bio-effects evaluation. However, at the end of the study (day 14), the Incision-Cath method had the lowest percentage of open wounds (4.2%), the smallest wound size (1.14 mm2), and the lowest percentage of tag loss (10%), and is likely the best method for transmitter implantation based on this pilot evaluation. Although the injection method had the fastest implantation time, and may allow cost-savings for telemetry studies with large sample sizes of tagged fish, the percentage of dropped tags (47.5%) was the highest of any treatment.

Tag loss and antenna loss for all implantation treatments was likely affected and biased by the kinking and tangling of the antenna material. At least 10 transmitter antennas were found to be tangled with each other, either within fish, or after tags had fallen out of fish. Further, the Injection, 9 smoother antenna coating would have likely reduced the implantation times of the Incision-Cath and 9 GA-Cath techniques due to jagged "barbs" of the coating that snagged on the surgery materials as the antenna was threaded through the 19-gauge needle. Tagging times were much faster (i.e., ~30 s) using uncoated transmitters on dead fish during our pre-experiment "practice" tagging. A smoother antenna coating or a different antenna material would also likely minimize the tangling of antennas in holding tanks following implantation, which is an important factor to consider for future field studies that necessitate holding fish in close proximity in small buckets. Standardizing the tag body size would also likely reduce the implantation times of the Injection technique. With a more consistent body size, the transmitter could be consistently loaded from the hub end, which resulted in tagging load times of about 5 s.

Improvements to surgical tools could also be beneficial for improving the tagging technique and reducing surgery time for the Injection and 9 GA-Cath techniques studied in this pilot evaluation. Modifications to the tubing used for the 9-gauge needle in the Injection technique could further reduce tag-loading time. Additionally, modification of the notched implanter used in the Injection technique could reduce implantation time by reducing antenna snags in the implanter during transmitter injection. The 9-gauge needle used in the 9 GA-Cath treatment was also cumbersome and designing a combination needle-implanter may improve tag retention, reduce wound size, and reduce implantation time.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect.

The invention claimed is:

1. A radio frequency transmitter comprising:
a body extending from a nose to a tail, the body housing a cylindrical battery and RF signal generator components, the cylindrical battery defining at least a portion of the nose of the body, and having a capacity of 6 mAh and being less than 6 mm long; and
an antenna extending from the tail.

2. The radio frequency transmitter of claim 1 wherein the battery comprises a Li/CFx micro-battery comprising a lithium metal anode and a carbon fluoride cathode.

3. The radio frequency transmitter of claim 1 wherein the antenna comprises Teflon PFA (perfluoroalkoxy)-coated stainless steel wire.

4. The radio frequency transmitter of claim 1 wherein the antenna defines a diameter of less than 38.1 µm and a length of less than 17.8 cm.

5. The radio frequency transmitter of claim 1 wherein the circular battery defines a diameter of less than 2.95 mm in at least one cross section.

6. The radio frequency transmitter of claim 1 wherein the circular battery defines a diameter of less than 12 mm in length.

* * * * *

UNITED STATES PATENT AND TRADEMARK OFFICE
CERTIFICATE OF CORRECTION

PATENT NO. : 10,236,920 B2
APPLICATION NO. : 15/087936
DATED : March 19, 2019
INVENTOR(S) : Z. Daniel Deng et al.

Page 1 of 2

It is certified that error appears in the above-identified patent and that said Letters Patent is hereby corrected as shown below:

On the Title Page

(56) References Cited: page 4, 1st column, 14th line:
Replace "DspaceEMIT: Innovation in Manufacturing Systems"
With --Dspace@MIT: Innovation in Manufacturing Systems--

(56) References Cited: page 4, 1st column, 45th line:
Replace "Barns, "Behavior and Swimming Performance of Elvers of the American Eel, Anguilla Rostrata, in an Experimental Flume", Journal of Fish Biology 45, 1994, United Kingdom, pp. 111-121."
With --Bams, "Differences in Performance of Naturally and Artificially Propagated Sockeye Salmon Migrant Fry, as Measured With Swimming and Predation Tests", Journal of the Fisheries Board of Canada 24(5), 1967, Canada, pages 1117-1153.--

(56) References Cited: page 4, 1st column, 71st line:
Replace "Atlantic Cod Inrapertoneatly Implanted with Dummy Acoustic"
With --Atlantic Cod Intraperitoneally Implanted with Dummy Acoustic--

(56) References Cited: page 4, 2nd column, 8th line:
Replace "Systems and Methods for Monitoring Organisma Within an Aquatic"
With --Systems and Methods for Monitoring Organisms Within an Aquatic--

(56) References Cited: page 4, 2nd column, 11th & 12th lines:
Replace "http://www.ti.com.lit/an/slua288.pdf"
With --http://www.ti.com/lit/an/slua288/slua288.pdf--

(56) References Cited: page 4, 2nd column, 15th line:
Replace "Canadian Science Advisory Secrerariat Science Advisory Report"
With --Canadian Science Advisory Secretariat Science Advisory Report--

Signed and Sealed this
Fifth Day of November, 2019

Andrei Iancu
*Director of the United States Patent and Trademark Office*

CERTIFICATE OF CORRECTION (continued)
U.S. Pat. No. 10,236,920 B2

(56) References Cited: page 4, 2nd column, 29th, 30th, 31st & 32nd lines:
Replace "MacGregor et al., "Recovery Strategy far the American Eel (Anguiiia reatrata) in Ontario". Ontario Recaveiy Strategy Series, Prepared for Ontario Ministry of Natural Resources, Peterboraagh, Ontario, 2013, Canada, 131 pages."
With --MacGregor et al., "Recovery Strategy for the American Eel (Anguilla rostrata) in Ontario", Ontario Recovery Strategy Series, Prepared for Ontario Ministry of Natural Resources, Peterborough, Ontario, 2013, Canada, 131 pages.--

(56) References Cited: page 4, 2nd column, 45th line:
Replace "Normandeau, "Survey for Upsteam American Eel Passage at Holyoke"
With --Normandeau, "Survey for Upstream American Eel Passage at Holyoke--

(56) References Cited: page 4, 2nd column, 53rd line:
Replace "Healing, Retention of Juvenile Chinook Salmon", Transactions of"
With --Healing, Survival, Growth, and Suture Retention of Juvenile Chinook Salmon", Transactions of--

(56) References Cited: page 4, 2nd column, 64th & 65th lines:
Replace "Performance Avoidance of Juvenile Chinook Salmon"
With --Performance and Predator Avoidance of Juvenile Chinook Salmon--